United States Patent
Bindschedler et al.

(10) Patent No.: US 11,180,606 B2
(45) Date of Patent: *Nov. 23, 2021

(54) METHOD FOR PRODUCING POLYESTER POLYOLS AND USE THEREOF IN POLYURETHANE

(71) Applicants: TEREOS STARCH & SWEETENERS BELGIUM, Aalst (BE); CENTRE NATIONAL DE LA RECHERCHE SCIENTIFIQUE, Paris (FR); SOCIÉTÉ SOPREMA SAS, Strasbourg (FR); UNIVERSITÉ DE STRASBOURG, Strasbourg (FR)

(72) Inventors: Pierre Etienne Bindschedler, Strasbourg (FR); Alexandru Sarbu, Strasbourg (FR); Stephanie Laurichesse, Strasbourg (FR); Remi Perrin, Strasbourg (FR); Pierre Furtwengler, Paris (RE); Luc Avérous, Paris (FR); Andreas Redl, Aalst (BE)

(73) Assignees: TEREOS STARCH & SWEETENERS BELGIUM, Aalst (BE); CENTRE NATIONAL DE LA RECHERCHE SCIEN'I'IFIQUE, Paris (FR); SOCIÉTÉ SOPREMA SAS, Strasbourg (FR); UNIVERSITÉ DE STRASBOURG, Strasbourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/327,542

(22) PCT Filed: Aug. 24, 2017

(86) PCT No.: PCT/IB2017/055107
§ 371 (c)(1),
(2) Date: Feb. 22, 2019

(87) PCT Pub. No.: WO2018/037371
PCT Pub. Date: Mar. 1, 2018

(65) Prior Publication Data
US 2019/0194380 A1 Jun. 27, 2019

(30) Foreign Application Priority Data

Aug. 24, 2016 (FR) ..................... 16/01253

(51) Int. Cl.
| | |
|---|---|
| *C08G 18/42* | (2006.01) |
| *C07C 67/08* | (2006.01) |
| *C07C 69/40* | (2006.01) |
| *C07C 69/44* | (2006.01) |
| *C08G 63/668* | (2006.01) |
| *C08K 5/00* | (2006.01) |
| *C08J 9/12* | (2006.01) |
| *C09D 175/04* | (2006.01) |
| *C09J 175/04* | (2006.01) |
| *C08G 18/76* | (2006.01) |
| *C08G 63/672* | (2006.01) |
| *E04B 1/74* | (2006.01) |

(52) U.S. Cl.
CPC .............. *C08G 18/42* (2013.01); *C07C 67/08* (2013.01); *C07C 69/40* (2013.01); *C07C 69/44* (2013.01); *C08G 18/4244* (2013.01); *C08G 18/7671* (2013.01); *C08G 63/668* (2013.01); *C08G 63/672* (2013.01); *C08J 9/125* (2013.01); *C08K 5/005* (2013.01); *C08K 5/0066* (2013.01); *C09D 175/04* (2013.01); *C09J 175/04* (2013.01); *C08G 2110/0008* (2021.01); *C08G 2110/0016* (2021.01); *C08G 2110/0025* (2021.01); *C08J 2375/04* (2013.01); *E04B 1/74* (2013.01)

(58) Field of Classification Search
CPC ......... C07C 67/08; C07C 69/40; C07C 69/44; C08G 18/42; C08G 18/4244; C08G 18/7671; C08G 63/668; C08G 63/672; C08G 2101/0008; C08G 2101/0016; C08G 2101/0025; C08J 9/125; C08J 2375/04; C08K 5/005; C08K 5/0066; C09D 175/04; C09J 175/04; E04B 1/74
See application file for complete search history.

(56) References Cited

U.S. PATENT DOCUMENTS

| | | | |
|---|---|---|---|
| 2,863,855 A | 12/1958 | Wilson et al. | |
| 2,980,650 A | 4/1961 | Wilson et al. | |
| 3,907,863 A * | 9/1975 | Voss ....................... | C08G 18/42 560/91 |
| 4,001,180 A | 1/1977 | Doyle et al. | |
| 4,404,295 A | 9/1983 | Bernstein et al. | |

(Continued)

OTHER PUBLICATIONS

International Search Report dated Oct. 17, 2017 in corresponding International application No. PCT/IB2017/055107; 5 pages.

(Continued)

*Primary Examiner* — John M Cooney
(74) *Attorney, Agent, or Firm* — Maier & Maier, PLLC

(57) ABSTRACT

A polyester polyol of formula produced by a first polycondensation (a) of a sugar alcohol Z in C3 to C8 and two diacids Y and Y' which are the same or different in C4 to C36, and a second polycondensation (b) of the product produced in (a) with two diols X and X' which are the same or different in C2 to C12, the polymer including such a polyester polyol. Also, a method for producing the polyester polyols and the use thereof in foams, adhesives, coatings or elastomers of polyurethane or polyisocyanurate.

21 Claims, 4 Drawing Sheets

(56) References Cited

U.S. PATENT DOCUMENTS

| | | | | |
|---|---|---|---|---|
| 4,469,823 | A | * | 9/1984 | Yeakey .............. C08G 18/4009 521/172 |
| 5,057,546 | A | | 10/1991 | Sudan |
| 5,605,940 | A | * | 2/1997 | Skowronski .............. B32B 5/18 521/172 |
| 2003/0020042 | A1 | * | 1/2003 | Wilson ..................... C08J 9/141 252/182.28 |
| 2006/0084709 | A1 | * | 4/2006 | Dobransky ........ C08G 18/4018 521/131 |
| 2012/0258269 | A1 | * | 10/2012 | Gehringer .............. C08G 18/08 428/36.9 |
| 2015/0218415 | A1 | * | 8/2015 | Nixon ................ C08G 18/4288 524/590 |
| 2015/0299373 | A1 | * | 10/2015 | Nefzger ................ C08G 18/42 521/119 |

OTHER PUBLICATIONS

Gustini, L. et al., "Enzymatic synthesis and preliminary evaluation as coating of sorbitol-based, hydroxy-functional polyesters with controlled molecular weights," European Polymer Journal, vol. 67, 2015, pp. 459-475.

Gustini, L. et al., "Green and selective polycondensation methods toward linear sorbitol-based polyesters: enzymatic vs. organic and metal-based catalysis," ChemSusChem, Issue 9, Jul. 13, 2016, pp. 2250-2260.

* cited by examiner

METHOD FOR PRODUCING POLYESTER POLYOLS AND USE THEREOF IN POLYURETHANE

FIELD

This invention relates to a method for obtaining polyester polyol, the polyester polyols obtained by the implementation of such a method, the use of such polyester polyols in the manufacture of foams, adhesives, coatings or polyurethane or polyisocyanurate elastomers.

BACKGROUND

Today, searching for products of renewable origin that can be substituted for petroleum-sourced products forms a strategy for the future in order to reduce our dependence on fossil resources. Polyurethanes are an important family of polymers, with strong demand for compounds with a bio-sourced origin. The industrial construction sector is looking for materials that are bio-sourced and sustainable, in particular in the field of foams that can be used for thermal and/or sound insulation. The uses of polyurethanes in this sector are substantially in the form of rigid foams, polyurethane (PUR) and polyisocyanurates (PIR).

Polyurethane materials (rigid and flexible foams, elastomers, coating, adhesive, etc.) are based on the reaction of a polyaddition between a polyisocyanate and a polyol. It therefore appears necessary to work on developing new materials that are increasingly competitive such as polyols of renewable origin comprised of synthons coming from biomass of which the production at high tonnage is possible.

Today, sorbitol is substantially used as a "starter" in the elaboration of polyether polyols by using a chemistry referred to as alkoxylation which is a relatively dangerous method in particular due to the reagents used. Alkoxylation is an industrial method of high temperature and pressurised chemistry that reacts alkylene oxides on a starter (sorbitol for example) in the presence of a catalyst thus creating polyether chains. This expensive and complex method furthermore uses dangerous reagents.

The second stake is also based on controlling the chemical modification of the sorbitol since the alkoxylation affects all of the hydroxyl functions of the sorbitol creating polyether polyols with a high functionality (typically 6). However, the polyurethane foam market is one of the consumer markets of polyether polyols and increasingly of polyester polyols. Furthermore, in the field of thermal insulation, a transition is observed in the market from polyurethane foams to polyisocyanurate foams with higher performance but which require new families of polyols with functionalities that are more reliable than those required during the elaboration of a polyurethane foam.

Sorbitol ($C_6H_{14}O_6$, 182.17 g/mol) also called D-glucitol (CAS No.: 50-70-4) or (2R,3R,4R,5S)-hexane-1,2,3,4,5,6 hexol is a reduced sugar coming from the hydrogenation of glucose; it is also naturally present in several fruits. Many chemical modifications are possible with sorbitol. Sorbitol has a solid and crystalline form at 23° C. However, for using sorbitol in polyols intended for the elaboration of polyurethane foams, the main chemical modifications are obtained via an oxypropylation reaction (Ionescu, *Chemistry and Technology of Polyols for Polyurethanes*) or polycondensation reaction.

Oxypropylation has been largely described in literature for more than 65 years (U.S. Pat. No. 2,605,233). This is an exothermic reaction that takes place in a closed reactor under pressure and is hot catalysed. This consists in the opening of a cycle that can be carried out under acid catalysis as well as basic catalysis, with the latter being used mostly (diagram 1). The reaction consists in the successive adding of molecules of propylene oxide ($C_3H_6O$) or of butylene oxide ($C_4H_8O$) on a starter molecule, carrying hydroxyl functions, able to be a sugar (US20140200327) or an oligo-polyol having a functionality between 2 and 6. In order to initiate the reaction, the reaction medium is heated to temperatures between 100° C. and 200° C., once the reaction is initiated, a violent elevation in the temperature and pressure is observed.

Schema 1: oxypropylation reaction

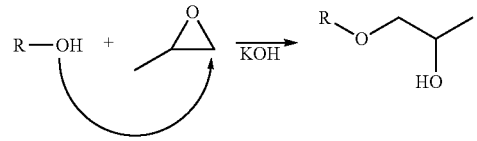

The first description of an oxypropylation reaction on sorbitol was described in 1958 by Joseph E. Wilson and Raymond H. Fowler (*Rigid Urethanes Foams Based on Sorbitol Derivatives Science*-1958-*WILSON*-1343) leading to polyols having a molar mass (Mn) between 760 and 4830 g·mol$^{-1}$ and a number of hydroxyls between 70 and 440 mg KOH/g. The number of hydroxyls being defined as a quantitative value of the number of hydroxyl groups that can react with a polyisocyanate expressed in milligrams of equivalent potassium hydroxide per gram of product. Much academic or industrial work describe techniques of oxypropylation, in particular those that make use of sorbitol as a starter molecule.

Polycondensation described for the first time by Carothers (*Wallace H. Carothers, J. if Am. Chem Soc.* 51, no. 8 (1929): 2548-59 and 2560-70) is a reaction between two molecules carrying each one a reactive function and of which the product of the reaction is comprised of the association of the two molecules and of the formation of a small molecule. In the case of polyesters, the reactive functions are an alcohol function typically, primary alcohols and an acid function. In this case, the small molecule coming from the reaction is a molecule of water (diagram 2).

Diagram 2: Reaction between an alcohol and an acid

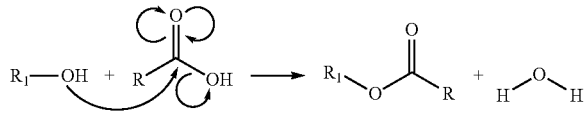

In order to obtain a polyester per se, the monomers used must at the minimum be diacids and diols so that the reaction is sustainable. In order to displace the equilibrium of the reaction in the direction of the product (polyester) and obtain higher molecular weights, the molecule of water created at each addition is eliminated. In order to increase the molar masses of the polymers obtained, the reaction can be catalysed. The two major families of catalysis are proton catalysis and catalysis via organometallic compounds to which is added enzyme catalysis which is increasingly used.

An example of the reaction of polycondensation catalysed by zinc acetate is described by Abhijeet Anand et al., (Abhijeet Anand et al *Progress in Organic Coatings* 74, no. 4 (August 2012): 764-67), between D-sorbitol, anhydrous 1,2,3,6 tetrahydrophtalic acid (THPA), diethylene glycol (DEG) and adipic acid. The reaction described and carried out in two steps, a first at 145-150° C. between the sorbitol, the THPA, the DEG and the zinc acetate for 1 h then the temperature is raised to 200° C. with the adding of adipic acid for 5-6 h. Polyester polyols with a molar mass of 1074 g·mol$^{-1}$ are then obtained. However, via infrared analysis a peak characteristic of a cyclic bond of the ether type at 1068 cm-1 attributed to the cyclisation of the sorbitol was observed. Such a cyclisation is linked to the high reaction temperature. This cyclisation of the sorbitol makes it unavailable for the reaction and therefore reduces the yield of the reaction.

Another polymerisation of the polycondensation type was studied by L. Gustini and. al. (L. Gustini et al., *a European Polymer Journal* 67 (June 2015): 459-75). This is polycondensation catalysed enzymatically with the enzyme candida antartica lipase B (CALB). The advantage of this enzyme is its selectivity for esterifying in priority the primary hydroxyls compared to the secondary hydroxyls and thus preventing any type of crosslinking during the polymer synthesis. However, the quantity of sorbitol incorporated is very low and not very pertinent since the enzyme CALB functions well only with apolar monomers (sorbitol is on the contrary highly polar). In order to counter this, the authors compensate the addition of sorbitol with a large quantity of apolar monomer (1.8 octanediol). Finally, the method proposes relatively complex syntheses and very long durations (in general more than 24 h). All of these limits make it a method that is difficult to use industrially.

Finally, a last type of similar polymerisation is proposed in patent application FR 2 987 840 filed by the company NOVANCE which describes the polycondensation between a fatty acid and sorbitol or glycerol in order to obtain polyesters. This method is also complex since a step of alkoxylation precedes the step of polycondensation. Furthermore, the temperatures applied are of 220° C. for relatively long reaction times from 15 to 20 h.

There is therefore a need for a simple and ecological method (without solvent, that uses bio-sourced products, at atmospheric pressure) and which makes it possible to obtain with high yield polyesters that can be used in particular in polyurethane polymers that have properties that are as good as those of the polymers obtained from products derived from petrol.

DETAILED DESCRIPTION

The invention relates to a polyester polyol obtained by a first polycondensation (a) of a sugar alcohol Z in C3 to C8 and of two diacids Y and Y' which are identical or different in C4 to C36 and of a second polycondensation (b) of the product obtained in (a) with two diols X and X' which are identical or different in C2 to C12.

The invention further relates to a polyester polyol having general formula Rx-Ry-Z-Ry'-Rx' wherein Z is a sugar alcohol in C3 to C8, preferably in C4 to C7, typically in C5, C6, Ry and Ry' are diesters having formula —OOC-Cn-COO— with n between 2 and 34, preferably, between 3 and 22, typically between 4 and 10, Rx and Rx' are monoalcohols, which are identical or different in C2 to C12, preferably in C3 to C8, typically in C4.

The term "polyester polyol" refers to molecules that comprise hydroxyl groups (diols or sugar alcohols) bonded together by ester bonds. Thus, in the polyester polyol according to the invention, the molecules X, Y, Z, Y' and X' are bonded together by ester bonds. Typically, the diols X and X' and the sugar alcohol Z are bonded to the two diacids Y and Y' by ester bonds each formed between an acid function of Y or of Y' and a primary hydroxyl function of Z, X or X'. Advantageously, the polyester polyol is of neutral pH, typically, when it is obtained by two successive polycondensations followed by a step of neutralisation (for example with potassium hydroxide or with sodium hydroxide).

The polyester polyol according to the invention advantageously has the general chemical formula $C_aH_bO_c$ with $22 \leq a \leq 42$, $38 \leq b \leq 78$, $14 \leq c \leq 22$.

Typically, the polyester polyol according to the invention has a molecular weight between 350 g/mol and 2000 g/mol, preferably between 420 g/mol and 1800 g/mol and more preferably, between 450 and 1700 g/mol. According to the invention, the molar mass of the polyester polyol can be determined by various methods such as steric exclusion chromatography.

Advantageously, the polyester polypol has a hydroxyl index from 300 to 900 mg KOH/g. The hydroxyl index (HOI) can be calculated with the following formula:

HOI=functionality of the polyester polyol×56109.37/Molar mass of the polyester polyol The hydroxyl index corresponds to the number of mg of KOH required to deprotonate all of the hydroxyl groups present in one gram of polyol. The hydroxyl index can be determined via inverse dosage using potash, for example according to the standard ASTM 4274-99 wherein the colorimetric titration is replaced with a pH-metric titration.

The term "sugar alcohol" or "polyol" means a hydrogenated form of monosaccharide of which the carbonyl group (aldehyde or ketone) has been reduced to a primary or secondary hydroxyl. Typically, sugar alcohol is chosen from glycerol, ethylene glycol, sorbitol, erythritol, xylitol, araditol, ribitol, dulcitol, mannitol and volemitol.

The term "diacid" means a carbon chain comprising two acid groups. According to the invention, the polyester polyol comprises two molecules Y and Y' of diacid. These molecules can be identical or different in C4 to C36, preferably C4 to C24. Typically, the two molecules of diacid are independently chosen from butanedioic acid (Succinic acid), pentanedioic acid (Glutaric acid), hexanedioic acid (Adipic acid), heptanedioic acid (Pimelic acid), octanedioic acid (Suberic acid), nonanedioic acid (Azelaic acid), decanedioic acid (Sebacic acid), undecanedioic acid, dodecanedioic acid, tridecanedioic acid (Brassylic acid), tetradecanedioic acid, pentadecanedioic acid, hexadecanedioic acid, fatty acid dimers having up to 36 carbons (C36) or mixture thereof. Typically, Y and Y' are diacids in C5 to C16 or C6 to C12. Advantageously, the preferred molecules of diacid are independently chosen from adipic acid and succinic acid.

The term "diol" means a carbon chain comprising two alcohol functions. According to the invention, the polyester polyol comprises two molecules X and X' of diols which are identical or different. Typically, the molecules of diol are independently chosen from 1,2 ethanediol, 1,3 propanediol, 1,4-butanediol, 1,6 hexanediol, 1,8 octanediol, 1,10 decanediol, 1,12 dodecanediol and mixtures thereof.

Advantageously, the polyester polyol according to the invention is chosen from bis(1,2 ethanediol)-sorbitol diadipate, bis(1,3 propanediol)-sorbitol diadipate, bis(1,4-butanediol)-sorbitol diadipate, bis(1,4-butanediol)-sorbitol diadipate modified with glycerol, bis(1,6 hexanediol)-sorbitol diadipate, bis(1,8 octanediol)-sorbitol diadipate, bis(1,10 decanediol)-sorbitol diadipate, bis(1,12 dodecanediol)-sorbitol diadipate, bis(1,4 butanediol)-sorbitol disuccinate and sorbitol-diadipate-sorbitol. Preferably, said polyester polyol is chosen from bis(1,8 octanediol)-sorbitol diadipate, bis(1,10 decanediol)-sorbitol diadipate and bis(1,4-butanediol)-sorbitol diadipate.

The invention also relates to a method for obtaining a polyester polyol according to the invention comprising the following steps:

a) a step of polycondensation at a temperature between 110 and 200° C., preferably, 120 to 180° C., more preferably, 130 and 170° C., typically 150° C., advantageously for 5 to 10 hours:
  i. of a sugar alcohol Z in C3 to C8, preferably in C4 to C7, advantageously in C5-C6, typically chosen from glycerol, sorbitol, erythritol, xylitol, araditol, ribitol, dulcitol, mannitol and volemitol,
  ii. of two diacids Y and Y' which are identical or different in C4 to C36, preferably in C5 to C24,
  iii. of two diols X and X' which are identical or different in C2 to C12, preferably in C3 to C8, typically in C4 advantageously, independently chosen from 1,2 ethanediol, 1,3 propanediol, 1,4-butanediol, 1,6 hexanediol, 1,8 octanediol, 1,10 decanediol, 1,12 dodecanediol, 1,4 butanediol and mixtures thereof, b) optionally, a step of neutralisation of the free acid functions in such a way as to bring back the polyester polyol to a neutral pH (pH=7), for example, via a base typically, a strong base such as sodium bicarbonate or potash, or via a weak base such as sodium carbonate, sodium bicarbonate, potassium carbonate or a mono- bi- or trialcohol in C4 to C8, such as hexanol; preferably the step of neutralisation is carried out by adding potassium carbonate or potash.

Advantageously, during the step of polycondensation, the diols X and X' and the sugar alcohol Z have a molar ratio (X+X')/Z between 1 and 3, preferably between 1.5 and 2.5 even more preferably between 1.8 and 2.2.

Typically during the step of polycondensation, the diacids Y and Y' and the sugar alcohol have a molar ratio (Y+Y')/Z between 1 and 3, preferably between 1.5 and 2.5 even more preferably between 1.8 and 2.2.

According to an embodiment, during the step of polycondensation, the diols X and X' and the diacids Y and Y' have a molar ratio (X+X')/(Y+Y') between 0.5 and 2, preferably between 0.7 and 1.5 even more preferably between 0.8 and 1.2.

Advantageously, the step of polycondensation comprises a first polycondensation (a) of the sugar alcohol Z and of the diacids Y and Y' and a second polycondensation (b) of the product obtained in (a) with the diols X and X'. This polycondensation in two steps makes it possible to obtain polyester polyol with this symmetrical structure. Typically, the diacids Y and Y' are identical and/or the diols X and X' are identical.

According to an embodiment, the sugar alcohol Z is mixed with the molecule or molecules of diacid Y and Y' then incubated for more than one hour, more preferably between 2 and 5 hours, even more preferably between 2.5 and 4 h, typically for 3 hours. The molecule or molecules of diol X and X' are added in a second step to the mixture then incubated for more than 4 hours, preferably, between 5 and 10 hours, typically, between 5.5 and 7 h. Preferably, the step of polycondensation is carried out in a vacuum.

Advantageously, during the step of polycondensation, the molecules of diacid Y and Y' react with the primary alcohols of the molecules of sugar alcohol Z then diols X and X'. The molecules of water coming from the reaction are recovered for the purpose of eliminating them.

The invention further relates to a polymer comprising the polyester polyol according to the invention, typically, said polymer is a polyurethane and/or a polyisocyanurate. Advantageously, the polymer according to the invention has a low rate of polymerisation from 2 to 10, this is referred to as a prepolymer. Such a prepolymer can then be present in a composition intended to form a foam, an adhesive, an elastomer or a coating. According to an embodiment, the polymer according to the invention has a high rate of polymerisation typically, greater than 10, such a polymer can then be present in a foam, an adhesive, an elastomer or a coating.

Advantageously, the polymer according to the invention comprises a molar mass greater than 1000 g/mol.

According to an embodiment, the polymer according to the invention has a molar mass between 1000 g/mol and 10,000 g/mol, preferably between 2000 g/mol and 7000 g/mol. Typically, the polymer is a prepolymer. Such a prepolymer during a step of polymerisation will give a non-crosslinked or crosslinked polymer.

According to another embodiment, the polymer according to the invention has a molar mass between $1.10^4$ and $1.7.10^6$ g/mol. Typically, the polymer is a non-crosslinked polymer.

According to another embodiment, the polymer according to the invention has a molar mass greater than $1.7.10^6$ g/mol. Typically, the polymer is a crosslinked polymer.

The term "polyurethane" means a polymer that comprises urethane functions, in other words, a urethane polymer. These polymers are substantially the result of the reaction of polyols in particular of the polyester polyol of the invention and of polyisocyanates. These polymers are generally obtained from formulations that have an index from 100 to 150 corresponding to an NCO/OH ratio between 1 and 1.5.

The term "polyisocyanurate" means the polymers resulting from the reaction of polyols in particular the polyester polyol of the invention and of polyisocyanates, which contain, in addition to urethane bonds, other types of functional groups, in particular triisocyanuric rings formed by the trimerisation of the polyisocyanates. These polymers, normally also called modified polyurethanes, are generally obtained from formulations that have an index 150-450, or an NCO/OH ratio between 1.5 and 4.5.

The term NCO/OH ratio means, in terms of this invention, the ratio between the number of NCO functions of the polyisocyanate and the number of OH functions of the sugar alcohol of the diol and of any other component comprising OH groups (water, solvents). The NCO/OH ratio is calculated with the following formula:

$$\text{NCO/OH ratio} = M_{exp}Pi \times ME\ Pi / M_{exp}\ SAI \times ME\ SAI$$

where:

$M_{exp}Pi$ is the mass of the polyisocyanate;
$M_{exp}SAI$ is the mass of the sugar alcohol;
ME SAI is the equivalent mass of the sugar alcohol and corresponds to the ratio between the molar mass of the sugar alcohol and the functionality of the sugar alcohol;
MEPi is the equivalent mass of the polyisocyanate and corresponds to the ratio between the molar mass of the polyisocyanate and the functionality of the polyisocyanate.

The invention also relates to a composition comprising said polyester polyol according to the invention or said polymer according to the invention. Advantageously, said composition is a foam, an elastomer, an adhesive, a coating or a composition that makes it possible to obtain any of the foam, elastomers, adhesives and coatings after polymerisation.

Typically, the composition according to the invention comprising said polyester polyol according to the invention or said polymer according to the invention in particular prepolymer, further comprises, a reaction catalyst, a polyisocyanate having a functionality at least equal to 2, optionally, a copolyol and additives.

The term "copolyol" means a compound carrying two hydroxyl functions (diol type) or more (polyol) added to the composition comprising the polyester polyol in order to adjust the properties thereof such as the functionality or the viscosity, to create crosslinking nodes or be a chain extender. The copolyols can be in C2 to C8, preferably in C3 to C7, advantageously in C4 to C6. The copolyols can advantageously be chosen from ethylene glycol, glycerol, sorbitol, erythritol, xylitol, araditol, ribitol, dulcitol, mannitol and volemitol. The preferred copolyols are glycerol and sorbitol.

Typically, the copolyol or copolyols are added in a polyester polyol/copolyol(s) ratio from 70/30 to 99/1, preferably, 75/25 to 95/5, even more preferably, 80/20 and 92/8, typically, 82/8 and 90/10, for example 85/15.

According to the invention, the composition comprises two copolyols typically a copolyol in C2 and a copolyol in C3 or a copolyol in C2 and a copolyol in C5 or a copolyol in C2 and a copolyol in C6 or a copolyol in C3 and a copolyol in C5 or a copolyol in C3 and a copolyol in C6 or a copolyol in CS and a copolyol in C6, or two copolyols in C3 or two copolyols in CS or two copolyols in C6.

Advantageously, the composition comprises at least one copolyol in C2, typically, two copolyols, for example a copolyol in C2 and a copolyol in C5 or C6, typically, ethylene glycol and glycerol, ethylene glycol and erythritol, ethylene glycol and xylitol, ethylene glycol and araditol, ethylene glycol and ribitol, ethylene glycol and dulcitol, ethylene glycol and mannitol or ethylene glycol and volemitol. According to the invention, the preferred mixture of copolyols is glycerol and ethylene glycol Advantageously, the composition comprises at least one copolyol in C3, typically, two copolyols, for example, a copolyol in C3 and a copolyol in C5 or C6, typically, glycerol and sorbitol, glycerol and erythritol, glycerol and xylitol, glycerol and araditol, glycerol and ribitol, glycerol and dulcitol, glycerol and mannitol or glycerol and volemitol. According to the invention, the preferred mixture of copolyols is glycerol and sorbitol.

Advantageously, the composition comprises at least one copolyol in C5 or in C6, typically, two copolyols, for example, a copolyol in C5 and a copolyol in C6 or two copolyols in C5 or in C6.

For example, the composition comprises two copolyols typically, erythritol and sorbitol, xylitol and sorbitol, araditol and sorbitol, ribitol and sorbitol, dulcitol and sorbitol, mannitol and sorbitol or volemitol and sorbitol.

Advantageously, the composition comprises two copolyols typically in a C3/C6 or C3/C5 or C5/C6 ratio between 95/05 to 50/50, preferably, 90/10 to 55/45, preferably 87/13 to 60/40, more preferably 85/15 to 62/38, even more preferably 80/20 to 65/35. According to the invention, the preferred ratio is 66/33, a ratio that is particularly advantageous in the framework of the of Glycerol copolyol/sorbitol mixture, in particular for a final polyester polyol/glycerol/sorbitol mixture of 85/10/5. The term "polyisocyanate" means any chemical compound comprising at least two separate isocyanate chemical functions (NCO), in other words, that have "a functionality at least equal to 2". When the polyisocyanate has a functionality of 2, this is referred to as di-isocyanate. The term functionality means, in terms of this invention, the total number of reactive isocyanate functions per molecule of isocyanate. The functionality of a product is evaluated via the titration of the NCO function by a method of return dosage of the excess dibultylamine by the chloridric acid. Typically, said polyisocyanate has a functionality between 2 and 5, typically between 2.2 and 4, preferably between 2.5 and 3.5 even more preferably between 2.7 and 3.3. Advantageously, said polyisocyanate is chosen from aromatic, aliphatic, cycloaliphatic polyisocyanates and mixtures thereof. Mention can be made for example of 2,4-toluene diisocyanate, 2,6-toluene diisocyanate, mixtures of 2,4- and 2,6-toluene diisocyanate, m-phenylene diisocyanate, p-phenylene diisocyanate, cis/trans of cyclohexane diisocyanate hexamethylene diisocyanate, m- and p-tetramethylxylylene-diisocyanate, m-xylylene, p-xylylene diisocyanate, naphthalene-m, m-diisocyanate, 1,3,5-hexamethyl mesitylene triisocyanate, 1-methoxyphenyl-2,4-diisocyanate, 4,4'-diphenyl-methane diisocyanate, 4,4'-diisocyanabiphenylene 3,3'-dimethoxy-4,4'-diphenyl diisocyanate, 3,3'-dimethyl-4,4'-diphenyl diisocyanate, 4,4",4"-triphenylmethane triisocyanate, toluene-2,4,6m-triisooyanate, 4,4'-dimethyl diphenyl methane-2,2', 5,5'-tetraisocyanate, and aliphatic isocyanates, such as hydrogenated 4,4'-diphenylmethane diisocyanate, hydrogenated toluene diisocyanate (TDI) and hydrogenated meta- and paraxylene diisocyanate of tetramethylxylylene diisooyanate (TMXDI®isooyanate, product of American Cyanamid co, Wayne, N.J., USA.), 3:1 meta-tetramethylxylylene diisocyanate/trimethylolpropane (Cythane 3160® isocyanate, from the company American Cyanamid Co.), plurifunctional molecules such as poly-diisocyanate of diphenylmethylene (pMDI) and the analogues thereof. Typically, the polyisocyanate is chosen from toluene diisocyanate (TDI), 4,4'-diphenylmethane diisocyanate (or 4,4'-diisocyanate of diphenylmethylene or 4,4'-MDI), polymethylene polyphenylene polyisocyanate (polymeric MDI, pMDI) and mixtures thereof.

The term "reaction catalyst" means a compound that introduced in a small quantity accelerates the kinetics of the formation of the urethane bond (—NH—CO—O—) by reaction between the polyester polyol of the invention and a polyisocyanate or activates the reaction between a polyisocyanate and water or activate the trimerisation of the isocyanates. Typically the reaction catalysts are chosen from tertiary amines (such as dimethylcyclohexane), derivatives of tin (such as tin dibutyldilaurate), ammonium salts (such as methanaminium N,N,N-trimethyl of 2,2-dimethylpropanoate), carboxylates of alkali metals (such as potassium 2-ethylhexanoate or potassium octoate) amine ethers (such as bis(2-dimethylaminoethyl) ether), and triazines (such as 1,3,5-Tris(3(dimethylamino)propyl))hexahydro-1,3,5-triazine).

Advantageously, a composition intended for the obtaining of a foam comprises said polyester polyol according to the invention or said polymer according to the invention in particular the prepolymer, a reaction catalyst, a polyisocyanate having a functionality at least equal to 2, a swelling agent and optionally, a stabiliser, a flame retardant.

Advantageously, when the composition is a foam or a composition that makes it possible to obtain a foam, the preferred polyester polyol is a polyester polyol with a neutral pH and/or comprises a sorbitol in terms of sugar-alcohol Z. Typically, the preferred polyester polyol is bis(1,2 ethanediol)-sorbitol-diadipate, bis(1,6 hexanediol)-sorbitol-diadipate or bis(1,4 butanediol)-sorbitol-diadipate, more preferably, bis(1,4 butanediol)-sorbitol-diadipate, or bis(1,6 hexanediol)-sorbitol-diadipate.

According to the invention, a foam comprises after polymerisation typically, a polymer according to the invention in particular a crosslinked polymer, a reaction catalyst, a swelling agent and optionally, a stabiliser, at least one copolyol.

Typically, the term "foam" as used for example in the expressions "polyurethane foam" or "polyisocyanurate foam", means a compound with a three-dimensional cell structure of the expanded type. Said foam can be rigid or flexible, with open or closed cells. Mention is made of rigid polyurethane (PUR), or rigid polyisocyanurate (PIR) for rigid polyurethane or polyisocyanurate foams.

The term "closed cell foam" means a foam of which the alveolar structure comprises walls between each cell that form a set of attached and separate cells allowing for the imprisonment of an expansion gas. A foam is qualified as a closed cell foam when it has a maximum of 10% of open cells. Typically, closed cell foams are mostly rigid foams.

The term "open cell foams" means a foam whose alveolar structure is formed of a continuous cell matrix with an open wall between the cells which do not allow for the imprisonment of an expansion gas. Such a foam allows for the creation of percolation paths within the cell matrix thereof. Typically, open cell foams are mostly flexible foams.

The term "swelling agent" means a compound that induces via a chemical and/or physical action an expansion of a composition during a step of foaming. Typically, the chemical swelling agent is chosen from water, formic acid, phthalic anhydride and acetic acid. The physical swelling agent is chosen from pentane and pentane isomers, hydrocarbons, hydrofluorocarbons, hydrochlorofluoroolfins, hydrofluoro-olefins (HFOs), ethers and mixtures thereof. Mention can be made of methylal as an example of a swelling agent of the ether type. According to the invention, a preferred mixture of chemical and physical swelling agent is for example a water/pentane isomer or formic acid/pentane isomer or water/hydrofluoro-olefin or pentane isomer/methylal/water or water/methylal mixture.

The term "stabilizer" means an agent that allows for the formation of an emulsion between the polyol and the swelling agent as well as the physical stability of the polymer matrix during the progress of the reactions in particular via the nucleation of the droplets of the swelling agent, the anti-coalescent stabilisation during the polymerisation. Typically, the stabilisers are chosen from any of the silicone glycol copolymers (for example Dabco DC198 or DC193 commercialised by Air Products), non hydrolysable silicone glycol copolymer (for example DC5000 from Air Products), polyalkylene siloxane copolymer (for example Niax L-6164 from Momentive), methylsiloxane polyoxyalkylene copolymer (for example Niax L-5348 from Momentive), polyetherpolysiloxane copolymer (for example Tegostab B8870 or Tegostab B1048 from Evonik), polydimethylsiloxane polyether copolymer (for example Tegostab B8526 from Evonik), polyethersiloxane (for example Tegostab 88951 from Evonik), a modified polyether-polysiloxane copolymer (for example Tegostab B8871 from Evonik), a polysiloxane polyoxyalkylene block copolymer (for example Tegostab BF 2370 from Evonik) and derivatives thereof or mixtures thereof.

The term "additives" means agents such as antioxidants (neutralisation agents of chain ends at the origin of the depolymerisation or co-monomer chains capable of stopping the propagation of depolymerisation), demoulding agents (talc, paraffin solution, silicone), anti-hydrolysis agents, biocides, anti-UV agents (titanium oxide, triazine, benzotriazole) and/or flame retardants (antimony, phosphorus, boron, nitrogen compounds).

The term "flame retardant" means a compound that has the property of reducing or preventing the combustion or the heating of the materials that it impregnates or covers, referred to as flame or fire retardant. Mention can be made for example alone or in a mixture, graphite, silicates, boron, halogenated or phosphorous derivatives such as Tris (1-chloro-2-propyl) phosphate (TCPP), triethyl phosphate (TEP), triaryl phosphate esters, ammonium polyphosphate, red phosphorous, trishalogenaryl, and mixtures thereof.

An example of a composition according to the invention that makes it possible to obtain a closed cell rigid foam is typically formulated with an index of 115 with is an NCO/OH ratio of 1.15. Typically, such a composition comprises at least 50 to 100 parts of a polyester polyol according to the invention, 0 to 50 parts of a copolyol, 150 to 500 parts of a polyisocyanate, 0.5 to 5 parts of a catalyst typically of an amine catalyst such as dimethylcyclohexylamine, 0.5 to 6 parts of a swelling agent such as water, 0 to 5 parts of a stabiliser such as a polyetherpolysiloxane copolymer and 0 to 20 parts of a flame retardant.

A closed cell rigid polyurethane foam comprises for example 100 parts of a polyester polyol, 270 parts of a polyisocyanate, 2 parts of an amine catalyst such as dimethylcyclohexylamine, 6 parts of a swelling agent such as water, 2.5 parts of a stabiliser such as a polyether-polysiloxane copolymer and 10 parts of a flame retardant.

An example of a composition that makes it possible to obtain a closed cell rigid polyisocyanurate foam is typically formulated with a minimum index of 200 or a minimum of 300 which is an NCO/OH ratio greater than 2.0 or greater than 3, preferably an index between 250 and 450, even more preferably between 300 and 400 which is an NCO/OH ratio preferably between 2.5 and 4.5, even more preferably between 3.0 and 4.0. A composition that makes it possible to obtain a closed cell polyisocyanurate rigid foam comprises, for example 50 to 100 parts of polyester polyol according to the invention, 0 to 50 parts of a copolyol, 150 to 500 parts of a polyisocyanate, 0.1 to 13 parts of at least one catalyst, preferably two catalysts, typically an amine catalyst and a potassium carboxylate (for example in an amine catalyst/potassium carboxylate ratio of 0.5 to 2), 0 to 20 parts of a swelling agent such as a pentane isomer, 0 to 8 parts of a stabiliser and 0 to 20 parts of a flame retardant.

Typically, a composition that makes it possible to obtain a closed cell polyisocyanurate rigid foam comprises for example, 100 parts of the polyester polyol according to the invention; 173 parts of a polyisocyanate such as polydiisocyanate of diphenylmethylene; 0.5 parts of an amine catalyst such as dimethylcyclohexane; 2.5 parts of a potassium carboxylate such as 2-ethylhexanoate of potassium; 18 parts of a swelling agent such as a pentane isomer; 2.5 parts of a stabiliser and 10 parts of a flame retardant.

Polyurethane or polyisocyanurate rigid foams are for example used as a rigid panel for thermal insulation typically, for buildings.

A composition that makes it possible to obtain a flexible polyurethane foam typically has an index from 100 to 120 and comprises for example 40 to 60% by weight of a polyester polyol according to the invention, 1 to 10% by weight of swelling agent typically water, 40 to 60% by weight of polyisocyanate such as toluene diisocyanate, 0 to 5% by weight of a stabiliser, 0.1 to 5% by weight of at least one catalyst.

A composition of flexible polyurethane foam comprises for example 100 parts of the polyester polyol according to the invention; 5 parts of swelling agent such as water; 50 parts of polyisocyanate such as toluene diisocyanate, 1 part of stabiliser such as Tegostab BF 2370; 0.2 parts of catalyst such as tin dibutyldilaurate.

Typically, flexible polyurethane foams are used for mattresses, automobile seats, furniture, sound insulation and acoustics.

The term "elastomer" such as in the expression "polyurethane elastomer" means a material that has elastic properties that can undergo great deformations and return to its initial state without loss of properties. A composition that makes it possible to obtain a polyurethane elastomer typically comprises a polyester polyol according to the invention or a polymer according to the invention typically, a prepolymer according to the invention, a polyisocyanate and at least one copolyol, preferably a diol, Typically, a composition that makes it possible to obtain a polyurethane elastomer has an NCO/OH ratio between 0.1 and 3; preferably between 0.5 and 2.

Advantageously, a composition that makes it possible to obtain an elastomer comprises 3 to 15% by weight of polyisocyanate such as 4,4'-diphenylmethane diisocyanate (4,4'-MDI), 25 to 75% by weight of a polymer of polyester polyol according to the invention with a molar mass preferably between 2000 and 6500 g/mol; 10 to 30% by weight of a copolyol typically, a diol such as a diol in C3 to C8. Advantageously, said polyester polyol forms the flexible segments of the elastomer, and the diol associated with the polyisocyanate the rigid segments of the elastomer.

The term "coating" such as in the expression "polyurethane coating" means a material intended to cover a surface for the purpose of protecting it, it can be for example this a resistant or thick in order to absorb impacts.

Typically, a composition that makes it possible to obtain a polyurethane coating, has an NCO/OH ratio greater than 1, preferably between 1.1 and 3.

An example of a composition that makes it possible to obtain a polyurethane coating comprises:

10 to 60% by weight of a polymer according to the invention typically, a prepolymer coming from the reaction between a polyester polyol of the invention preferably with a molar mass 2000 g/mol and a polyisocyanate such as 4,4'-MDI; the NCO/OH polymer ratio according to the invention being >1 typically the ratio being between 1.1 and 3, 0 to 5% by weight of pigments or of pigment paste, such as for example azo pigments, 0 to 2% by weight of a catalyst for example dibutyltin dilaurate (DBTDL)

optionally, 0 to 5% of additives such as for example:

0 to 5% by weight of rheological additives such as for example reactive solvents or diluents, or thickeners;

0 to 5% by weight of functional additives such as anti-foam agents, anti-fungal agents or the mixture thereof.

The term "rheological additives" means additives that have for function to increase or reduce the viscosity of the composition, this is solvents, diluents or thickener, mention can be made for example of ethylene glycol.

The term "functional additives" means compounds that provide the composition with a particular functionality such as anti-foam agents and in particular polysiloxane polyethers such as Tergitol L (Dow), anti-fungal agents such as for example pentachlorophenol.

Advantageously, the polymerisation of the composition including the prepolymer according to the invention starts after the application of said coating composition on a support in order to obtain a crosslinked coating. Typically, the polymerisation reaction is carried out with the humidity of the air.

The term "adhesive" or "adhesive composition" means a composition allowing for the adhesion between two compounds, surfaces or objects, an example of an adhesive composition includes a polyester polyol of the invention, a polyisocyanate with an NCO/OH ratio between 1 and 1.6 and a catalyst such as tin dibutyldilaurate typically, at 0.05% w/w.

The invention also relates to a method for obtaining a foam, a coating, an adhesive or a polyurethane or polyisocyanurate elastomer comprising a step of obtaining a polyester polyol according to the invention or of a polymer according to the invention in particular a prepolymer according to the invention, a step of adding at least one polyisocyanate, at least one swelling agent, a stabiliser and at least one reaction catalyst, and a step of polymerisation and optionally a flame retardant.

The invention finally relates to the use of a polyester polyol according to the invention advantageously chosen from bis(1,2 ethanediol)-sorbitol diadipate, bis(1,3 propanediol)-sorbitol diadipate, bis(1,4-butanediol)-sorbitol diadipate, bis(1,6 hexanediol)-sorbitol diadipate, bis(1,8 octanediol)-sorbitol diadipate, bis(1,10 decanediol-)sorbitol diadipate, bis(1,12 dodecanediol)-sorbitol diadipate, bis(1,4 butanediol)-sorbitol disuccinate, or sorbitol-diadipate-sorbitol in the manufacture of a foam, of a coating, of an adhesive or of a polyurethane or polyisocyanurate elastomer.

Although they have distinct meanings, the terms "including", "containing", "comprising" and "consisting of" have been used interchangeably in the description of the invention, and can be replaced with one another. The invention shall be better understood when reading the following figures and examples given solely for the purposes of information.

EXAMPLES

Example 1

Figure 1A:
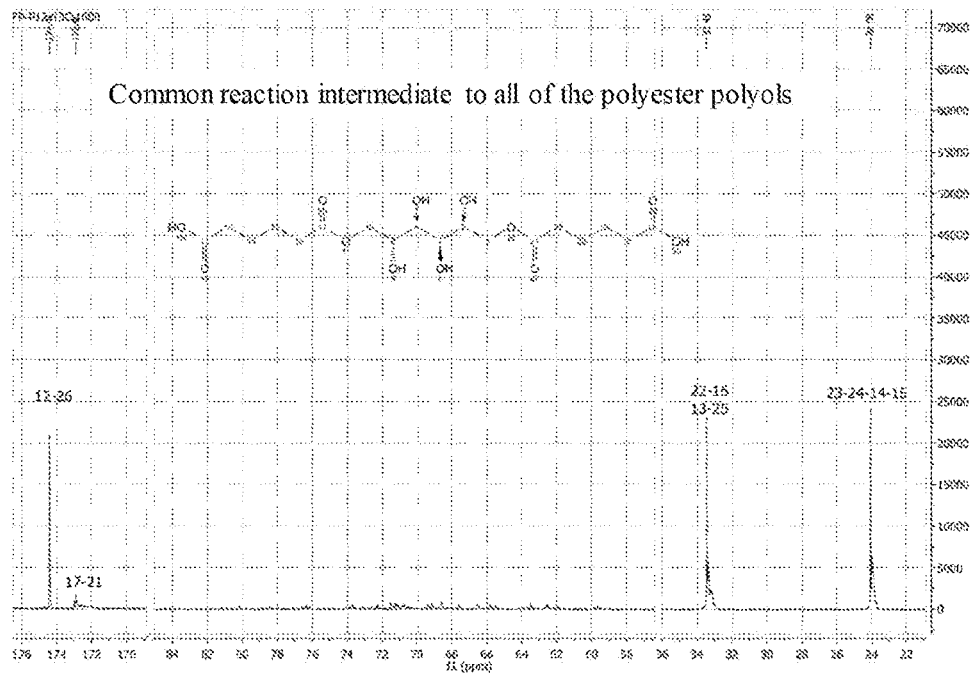
FIG. 1a corresponds to the spectra of NMR 13C of the bi-acidic reaction intermediate common to all of the polyester polyols where Y=Y'=adipic acid.

1.1 Equipment and Methods:

The D-sorbitol commercialised by TEREOS SYRAL (sorbitol sup. 98%, water less 0.5%, reducing sugars less 0.1%); 1,4 butanediol (99%), 1,10 decanediol, 1,2-ethanediol, 1,6-hexanediol, 1,10-octanediol, 1,12-dodecanediol are commercialised by the company SIGMA ALDRICH; 1,8 octanediol (98%) and Glycerol are commercialised by the company FLUKA; adipic acid (99%) commercialised by the company ACROS ORGANICS; 1,3-propanediol by ALFA AESAR and succinic acid (Technical grade) commercialised by the company BIOAMBERT.

The sorbitol and the adipic acid are dried in an oven at reduced pressure at 45° C. for one night then are stored in a vacuum desiccator. The other products are used as is.

Synthesis of bis(1,2 ethanediol)-sorbitol diadipate (bis(2-hydroxylethyl) O,O'-((2R,3R,4R,5S)-2,3,4,5-tetrahydroxyhexane-1, 6-diyl) diadipate)

In a three-neck flask (three necks with lapping 29:32) of 250 mL, 10.00 g of sorbitol (0.0549 mol) and 16.03 g of adipic acid (0.11 mol) are introduced. The entry of argon is fixed on the first neck of the three-neck flask, on the second (central neck) is fixed the complete short column distillation system. Finally the third and last neck is plugged using a plug of the septum type that is perforable in order to allow for future injections into the reaction medium. The reaction medium is brought to 150° C. under inert atmosphere (argon) and under a low stirring set to 100 rotations per minute (rpm) which will be increased to 350 rpm once the reaction medium is entirely viscous. After three hours of reaction, 6.83 g of 1,2-ethanediol (0.11 mol) are injected using a 12 mL syringe then the reaction is continued for 6 h for a total reaction time of 9 h. At 8 h00 and 9 h00 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,3-propanediol)-sorbitol diadipate (bis(3-hydroxypropyl) O,O'-((2R,3R,4R,5S)-2,3,4,5-tetrahydroxyhexane-1, 6-diyl) diadipate)

In a 250 mL three-neck flask 2.00 g of sorbitol (0.0110 mol), 3.2 g of adipic acid (0.0219 mol) and a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 1.67 g of 1,3-propanediol (0.0219 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,4-butanediol)-sorbitol diadipate (bis(4-hydroxybutyl)O,O'-((2R,3R,4R,5S)-2, 3, 4, 5-tetrahydroxyhexane-1, 6-diyl) diadipate)

In a 250 mL three-neck flask, 10.00 g of sorbitol (0.0549 mol) and 16.03 g of adipic acid (0.11 mol) as well as a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 9.98 g of 1,4-butanediol (0.11 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,6 hexanediol)-sorbitol diadipate (bis(6-hydroxyhexyl)O,O'-((2R,3R,4R,5S)-2,3,4,5-tetrahydroxyhexane-1, 6-diyl) diadipate)

In a 250 mL three-neck flask, 2.00 g of sorbitol (0.0110 mol) and 3.2 g of adipic acid (0.0219 mol) as well as a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 9.98 g of 1,6hexanediol (0.0219 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,8 octanediol)-sorbitol diadipate (bis(8-hydroxyoctyl) O,O'-((2R,3R,4R,5S)-2,3,4,5-tetrahydroxyhexane-1,6-diyl) diadipate)

In a 250 mL three-neck flask are introduced 1.000 g of sorbitol (0.00549 mol), 1.603 g of adipic acid (0.01098 mol) as well as a magnetic stirrer. The mounting of the three-neck flask and of the distillation system is carried out as hereinabove. The reaction medium is brought to 150° C. under inert atmosphere (argon) and under a low stirring at 100 rpm then at 350 rpm once the reaction medium is entirely viscous. After three hours of reaction, 1.605 g of 1,8-octanediol (0.01098 mol) is injected then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,10 decanediol)-sorbitol diadipate (bis(10-hydroxydecyl) O,O'-((2R,3R,4R,5S)-2,3,4,5-tetrahydroxyhexane-1,6-diyl) diadipate)

In a 250 mL three-neck flask, 1.000 g of sorbitol (0.00549 mol) and 1.603 g of adipic acid (0.01098 mol) as well as a magnetic stirrer are introduced. The mounting of the three-neck flask and of the distillation system is carried out as hereinabove. The reaction medium is brought to 150° C. under inert atmosphere (argon) and under a low stirring at 100 rpm then at 350 rpm once the reaction medium is entirely viscous. After three hours of reaction, 1.910 g of 1,10-octanediol (0.01098 mol) is injected then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,12 dodecanediol)-sorbitol diadipate (bis(12-hydroxydodecyl) O,O'-((2R,3R,4R,5S)-2,3,4,5-tetrahydroxyhexane-1,6-diyl) diadipate)

In a 250 mL three-neck flask, 5.00 g of sorbitol (0.0274 mol) and 8.015 g of adipic acid (0.0549 mol) as well as a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 11.089 g of 1,12-dodecanediol (0.0549 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,4 butanediol)-sorbitol disuccinate (bis(4-hydroxybutyl) O,O'-((2R,3R,4R,5S)-2,3,4,5-tetrahydroxyhexane-1,6-diyl) disuccinate)

In a 250 mL three-neck flask, 10.00 g of sorbitol (0.0549 mol) and 12.95 g of succinic acid (0.11 mol) as well as a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 9.98 g of 1,4-butanediol (0.11 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of sorbitol-diadipate-disorbitol (2S,3R,4R,5R)-2,3,4,5,6-pentahydroxyhexyl ((2R,3R,4R,5S)-2,3,4,5-tetrahydroxy-6-((6-oxo-6-(((2R,3R,4R,5S)-2,3,4,5,6-pentahydroxyhexyl)oxy) hexanoyl)oxy)hexyl) adipate In a 250 mL three-neck flask, 10.00 g of sorbitol (0.0549 mol) and 16.03 g of adipic acid (0.11 mol) as well as a magnetic stirrer are introduced. The mounting of the three-neck flask and of the distillation system is carried out as hereinabove. The reaction medium is brought to 150° C. under inert atmosphere (argon) and under a low stirring set to 100 rpm which will be increased to 350 rpm once the reaction medium is entirely viscous. After three hours of reaction, 20.0 g of sorbitol (0.11 mol) are injected using a 12 mL syringe then the reaction is continued for 6 h which is a total reaction time of 9 h. At 3 h30 and 6 h30 of reaction two passages under vacuum of respectively 30 seconds and 1 minute are carried out in order to draw the water produced by the polycondensation reaction. After each passage in the vacuum, the reaction medium is brought under inert atmosphere and to atmospheric pressure.

Synthesis of bis(1,4-butanediol)-sorbitol diadipate (bis(4-hydroxybutyl)O,O'-((2R,3R,4R,5S)-2,3,4,5-tetrahydroxyhexane-1,6-diyl) diadipate) and 1,4-butanediol-sorbitol adipate modified in reactor The reaction is carried out in a stainless steel sealed reactor equipped with a U-shaped stirring blade, with a Dean Stark having an outlet at the top of the condenser in order to connect thereto a vacuum pump and a low outlet in order to recover the condensates, an inlet and an outlet for inert gas. Into the reactor are introduced in the powder state sorbitol and adipic acid in a molar ratio of 1/2 (sorbitol/adipic acid). The reactor is placed under inert atmosphere then is turned on for heating. When the temperature reaches 100° C., the stirring is progressively started up to 170 rpm. When the temperature reached 150° C., the reaction is started and continued for 3 h. After 3 h, 1,4 butanediol (called diol in what follows) is introduced into the reactor in a molar ratio (1,4 butanediol/sorbitol) of 2.2/1. When the temperature of the reaction medium returns to 150° C. (stirring still maintained at 170 rpm, inert atmosphere) the diol is added after 2 h30 then a passage under partial vacuum is carried out for a duration of one minute then the atmospheric pressure is brought under inert atmosphere. 4 h30 after the adding of diols, another partial vacuum flush is carried out for 2 minutes then the atmospheric pressure if brought under inert atmosphere. 6 h15 minutes after the introduction of the diol (which is a total reaction time of 9 h15 min at 150° C.), the reactor is stopped and the reaction product is recovered hot in order to have a minimum of loss during the transfer of the material from the reactor to the packaging of the product.

1.2 Preparation of Samples for Measuring the Hydroxyl Index (HOI)

The measuring of the hydroxyl index was carried out according to the standard ASTM 4274-99 wherein the calorimetric titration was replaced with a pH-metric titration. More particularly, the measurement was carried out in the following way. In a 250 mL one-neck flask, about 1 g of sample us weighed to the nearest 1 mg.

20 mL of a reactive solution of phthalic anhydride 1N in the pyridine are added using the 20 mL gauged pipette then the system is set to reflux for 45 min at 130° C. After having cooled the mixture, 10 mL of pyridine are introduced from the top of the coolant then the contents of the flask is transferred into a 150 mL tall beaker for titration. Then 20 mL of pyridine and 30 mL of water are added before titrating via potash in the water at 1N using the automatic titrator.

1.3 Preparation of Samples for the NMR $^{31}$P Analysis

About 10-15 mg of polyol are introduced into a 4 mL flask to which is added 400 μL of solvent (pyridine/CDCl$_3$ ratio 1.6/1, v/v), the mixture is left under magnetic stirring for 2 min. Then are added 100 μL of a standard solution (1 mmol of N-hydroxylnaphthalimide in 10 mL of solvent and 50 mg of Cr(III) acetyl acetonate) and 100 μL of phosphorous reagent (2-chloro-1,2,3-dioxaphospholane). The whole is left under magnetic stirring at ambient temperature for 2 h before the analysis $^{31}$P NMR.

1.4 Neutralisation of the Polyols with a Sorbitol Base

As the polycondensation reaction during the synthesis of the various polyols does not make it possible to reach conversion rates of 100% residual traces of unreacted acid are then found in the final product. In order to overcome this, three types of neutralisation were considered. Two conventional neutralisations of the acido-basic type with soda or with potash in order to neutralise the acid residue via a simple acido-base reaction and a neutralisation via hexan-1-ol or an esterification via a mono-alcohol.

a) Neutralisation via soda (NaOH)

In a 250 mL single-neck flask are introduced: 50.4 g of 1,4 butanediol-sorbitol adipate, 2.065 g of NaOH corresponding to the residual acidity to be neutralised (determined by titration) as well as 60 mL of ethanol in order to fluidify the medium. The flask is provided with a bulb condenser and the medium is heated to 60° C. The reaction time is one hour. The reaction product is then distilled with a distillation bridge in order to extract the ethanol and recover the neutralised initial polyol.

b) Neutralisation via potash (KOH)

In a 250 mL single-neck flask are introduced: 49.9 g of 1,4 butanediol-sorbitol adipate, 2.89 g of KOH corresponding to the residual acidity to be neutralised (determined by titration) as well as 60 mL of ethanol in order to fluidify the medium. The flask is provided with a bulb condenser and the medium is heated to 60° C. The reaction time is one hour. The reaction product is then distilled with a distillation bridge in order to extract the ethanol and recover the neutralised initial polyol.

c) Neutralisation with hexanol

In a 250 mL single-neck flask are introduced: about 23.3 g of 1,4 butanediol-sorbitol adipate, as well as 170 mL of hexanol. The flask is provided with a distillation bridge which allows for the reflux of the hexanol and the elimination of the water produced by the reaction then the medium is brought to reflux for one night. The reaction product is then vacuum distilled at 130° C. with a distillation bridge.

1.5 Characterisation of the Products Obtained

The molar masses and the polydispersity indexes were determined by steric exclusion chromatographies in the chloroform by using a Shimadzu liquid chromatography. The columns used are PLGel Mixed—This PLGeL of 100A. A refraction index differential detector is used. Chloroform is used as an eluent at a flow rate of 0.8 ml/min. The device is calibrated with linear polystyrene standards with molar masses ranging from 162 to 1,650,000 g/mol.

The calculations of the mean molecular weights and of the polymolecularity indexes in RI or UV detection are carried out according to a calibration curve with polystyrene or polymethylmethacrylate standards.

The thermogravimetric analyses (ATG) were carried out on a TGA Q5000 from TA Instrument and the analyses were carried out using the Universal Analysis 2000 software. The heat ramp is set to 10° C./min from 25° C. to 600° C. under a constant flow of reconstituted air or of helium at 25 mL/min.

The differential scanning calorimetry analyses (DSC) are carried out using a DSC Q200 from TA Instrument. The heat ramps are set to 10° C./min and the cooling ramps at 5° C./min between −85° C. and 160° C. under a flow of $N_2$ adjusted to 25 mL/min. The data is analysed using the Universal Analysis 2000 software.

The return titrations are carried out using an automatic TitroLine 7000 titrator supplied by SI Analitics. The titrating solution used is obtained from volume concentrates (Fixanal) supplied by Fluka Analytical.

The magnetic resonance of the phosphorous ($^{31}P$) was carried out on a Bruker advance 3 400 MHz spectrometer. The spectral window is centred on 22677 Hz and is 100 ppm wide (particles per million). The relaxation time is set to 2 seconds and the number of scans recorded is 128.

The magnetic resonance of the proton was carried out on the same spectrometer with a number of scans of 128.

The infrared spectroscopy was carried out with a Nicolet 380 Fourier transform infrared spectrometer (Thermo Electron Corporation). The device is equipped with a module for analysing the attenuated total reflection (ATR) on diamond with a resolution of 4 $cm^{-1}$, 64 analysis scans per sample with an ATR correction proper to the diamond are carried out.

The rheological measurements were taken on an Anton Paar Physica MCR 301 rheometer with a plane cone geometry of 25 mm in diameter and a Peltier effect enclosure. The analysis program is comprised of three steps:

1: a temperature ramp from 0° C. to 50° C. at 0.1° C./min and a constant shear rate of 10 $s^{-1}$ 2: a scanning at a shear rate ranging from 0.001 $s^{-1}$ to 100 $s^{-1}$ at a constant temperature of 20° C.

3: a scanning at a shear rate ranging from 0.001 $s^{-1}$ to 100 $s^{-1}$ at a constant temperature of 25° C.

Example 2

Results 2.1 Analysis of the Structure of the Products Obtained and Yields

The synthesis methods implemented made it possible to obtain the following 9 molecules:

bis(1,4 butanediol)-sorbitol disuccinate
sorbitol-diadipate-sorbitol
bis(1,2 ethanediol)-sorbitol diadipate
bis(1,3 propanediol)-sorbitol diadipate
bis(1,4 butanediol)-sorbitol diadipate
bis(1,6 hexanediol)-sorbitol diadipate
bis(1,8 octanediol)-sorbitol diadipate
bis(1,10 decanediol)-sorbitol diadipate
bis(1,12 dodecanediol)-sorbitol diadipate The method according to the invention makes it possible to obtain the products hereinabove with yields between 80 and 90%. The synthesised products have different macroscopic aspects for example:

bis(1,2 ethanediol)-sorbitol diadipate: slightly yellow viscous liquid
bis(1,3 propanediol)-sorbitol diadipate: slightly yellow viscous liquid
bis(1,4 butanediol)-sorbitol diadipate: slightly yellow viscous liquid
bis(1,6 hexanediol)-sorbitol diadipate: yellowish solid gel
bis(1,8 octanediol)-sorbitol diadipate: orangish wax
bis(1,10 decanediol)-sorbitol diadipate: whitish wax
bis(1,12 dodecanediol)-sorbitol diadipate: beige wax 2.1.1 Analysis in Fourier Transform Infrared Spectroscopy (FT-IR)

The bis(1,2 ethanediol)-sorbitol diadipate, bis(1,3 propanediol)-sorbitol diadipate, bis(1,4-butanediol)-sorbitol diadipate, bis(1,6 hexanediol)-sorbitol diadipate, bis(1,8 octanediol)-sorbitol diadipate, bis(1,10 decanediol)-sorbitol diadipate, bis(1,12 dodecanediol)-sorbitol diadipate, were analysed by FT-IR.

For each product the characteristic absorption bands of the hydroxyl functions (wide band at 3999 $cm^{-1}$), carbon chains (absorption band at 2940 $cm^{-1}$) and the band that corresponds to the ester functions (thin and intense band at 1725 $cm^{-1}$) were observed. The presence of these absorption bands, more particularly those of the ester function confirms that the esterification function did indeed take place and that the structure of the polyols is indeed of the polyester polyol type carrying hydroxyl functions required for the formulation of PUR and PIR foam.

No reaction co-product comes from the FT-IR analysis, the residual acid functions cannot be seen in FT-IR as they are confounded in the bottom of the characteristic absorption band of the ester functions. Compared to the methods of prior art, the method of this invention does not induce or induces very little cyclisation of the sorbitol. Indeed, no absorption band at 1068 cm$^{-1}$ characteristic of the cyclisation of the sorbitol is observed. It is however possible that these cyclisation phenomena are present as a minority and therefore undetectable because less than the detection limit of the method used, or due to the superposition of the signal concerned among other absorption bands in the zone between 1500 and 940 cm$^{-1}$.

2.1.2 Analysis of the Results via NMR of the Proton (NMR-$^1$H)

The magnetic resonance analysis of the proton of all of the synthesised polyols allows the progress of the reaction to be followed by following the change in the peak corresponding to the proton in α of the ester bond formed at 2.3 ppm and that of the proton in α of the acid function consumed at 2.2 ppm. This makes it possible to determine the various characteristics times of the esterification reactions at play. During the first portion of the synthesis when the relative intensity of the peak corresponding to the acid function has decreased by half, the reaction intermediate sought is obtained with a yield of 100% and corresponds to the moment of injection of the terminal diol. At the end of the reaction, the ratio of the two peaks provides information on the state of progress of the reaction between the reaction intermediate and the diol. The maximum progress reached is 85%.

2.1.3 Analysis of the Results via NMR of the Carbon (NMR-$^{13}$C)

The magnetic resonance analysis of the carbon makes it possible to assign all of the carbon atoms present in the molecule to a chemical shift. This analysis makes it possible to determine the carbon skeleton of the various synthesised polyols. The ranges of chemical shifts used as a reference for the analysis of the various spectra are as follows:

TABLE 1

Chemical shifts of the various carbons present in the polyester polyols

| Chemical shifts in ppm | Corresponding carbon |
| --- | --- |
| 23 to 26 | Non-functionalised carbon chains |
| 27 to 35 | Carbon chains in the vicinity of ester or alcohol functions |
| 60 to 62 | Carbon carrying a terminal primary hydroxyl function |
| 62 to 64 | Carbon in α of the ester on the sorbitol chain |
| 64 to 75 | Carbon chain of the sorbitol (low signal) |
| 172 to 173 | Carbonyl |

Figure 1B:
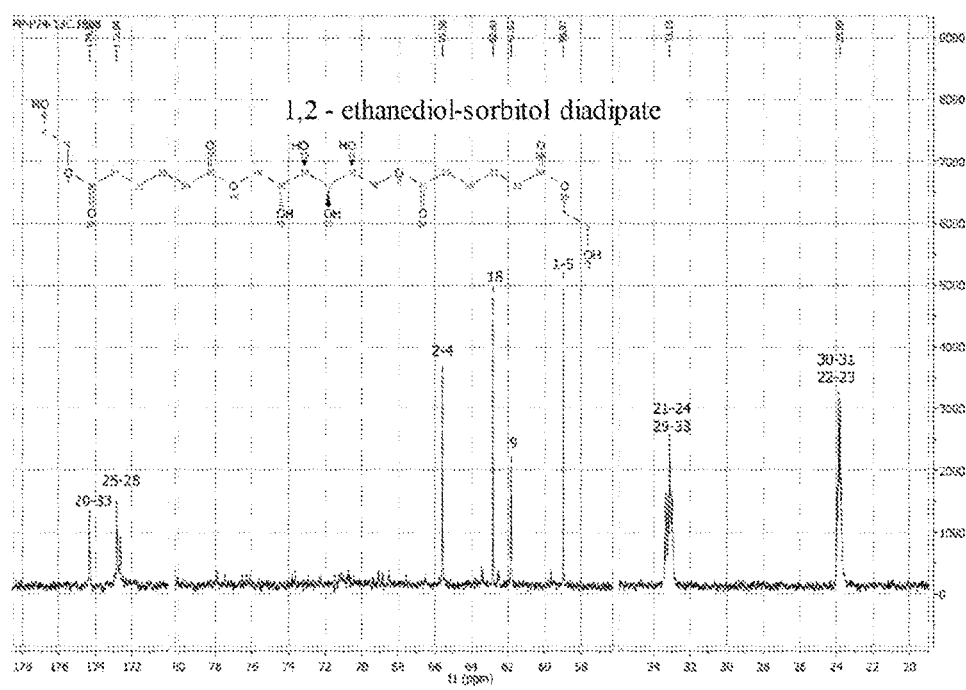
FIG. 1b corresponds to the spectrum of NMR 13C of bis (1,2 ethanediol)-sorbitol diadipate.
Figure 1C:
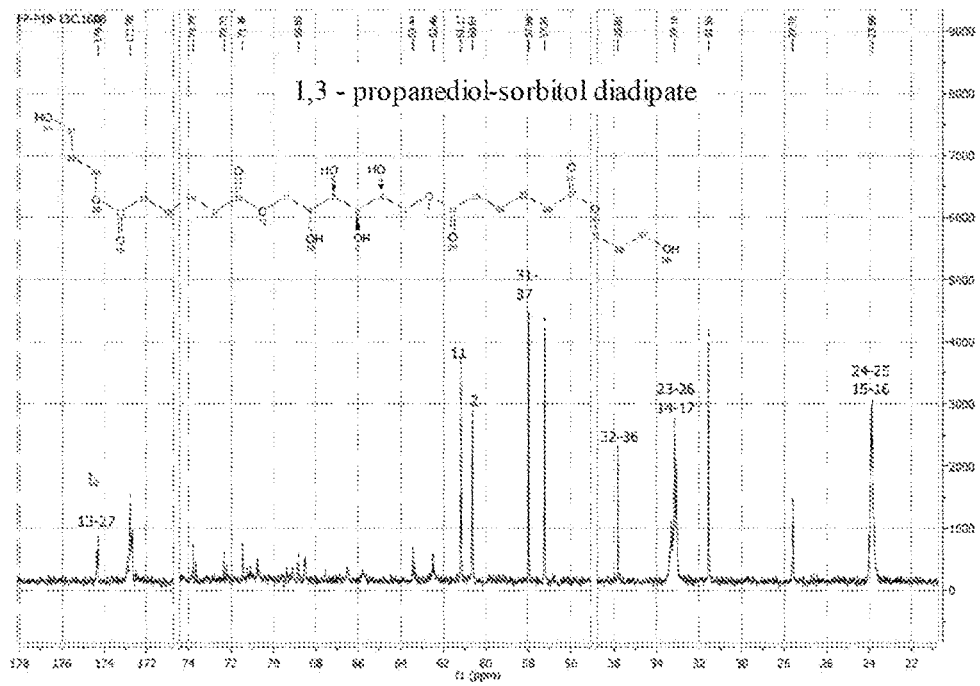
FIG. 1c corresponds to the spectrum of NMR 13C bis(1, 3-propanediol)-sorbitol diadipate.
Figure 1D:
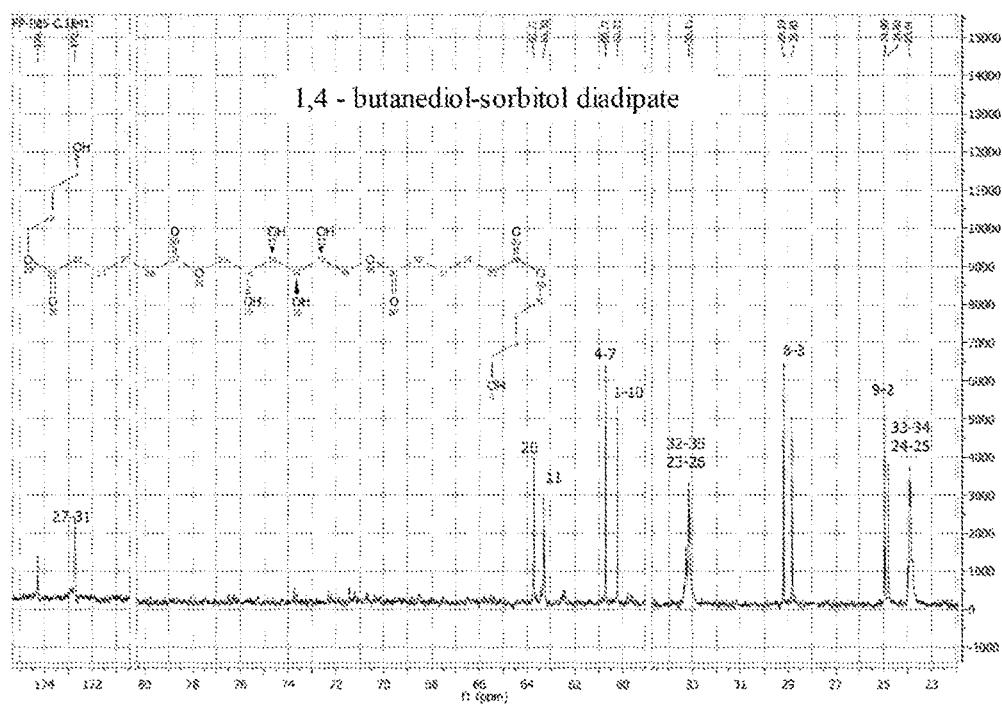
FIG. 1d corresponds to the spectrum of NMR 13C bis(1, 4-butanediol)-sorbitol diadipate.
Figures 2A, 2B:
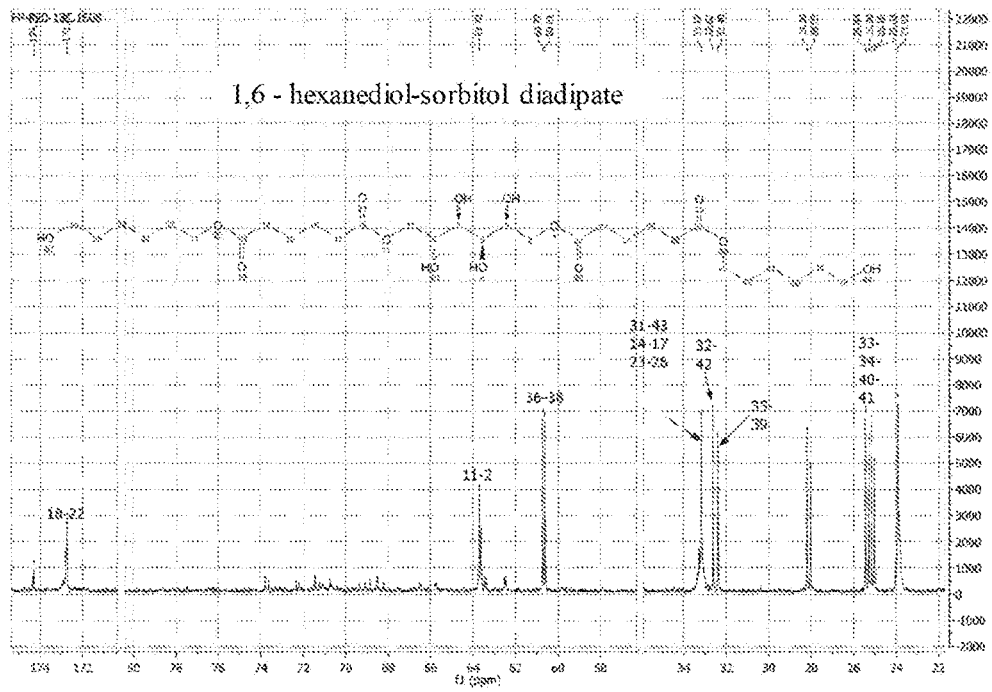
FIG. 2a corresponds to the spectrum of NMR 13C bis (1,6 hexanediol)-sorbitol diadipate.
FIG. 2b corresponds to the spectrum of NMR 13C bis (1,8 octanediol)-sorbitol diadipate.
Figure 2C:
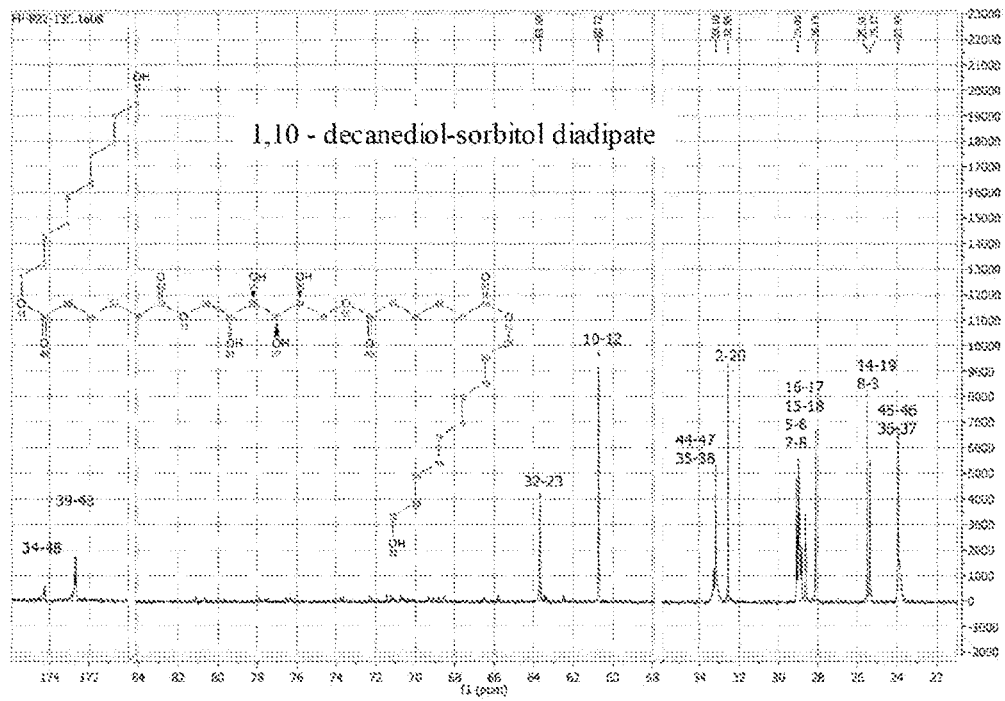
FIG. 2c corresponds to the spectrum of NMR 13C bis (1,10 decanediol)-sorbitol diadipate.
Figure 2D:
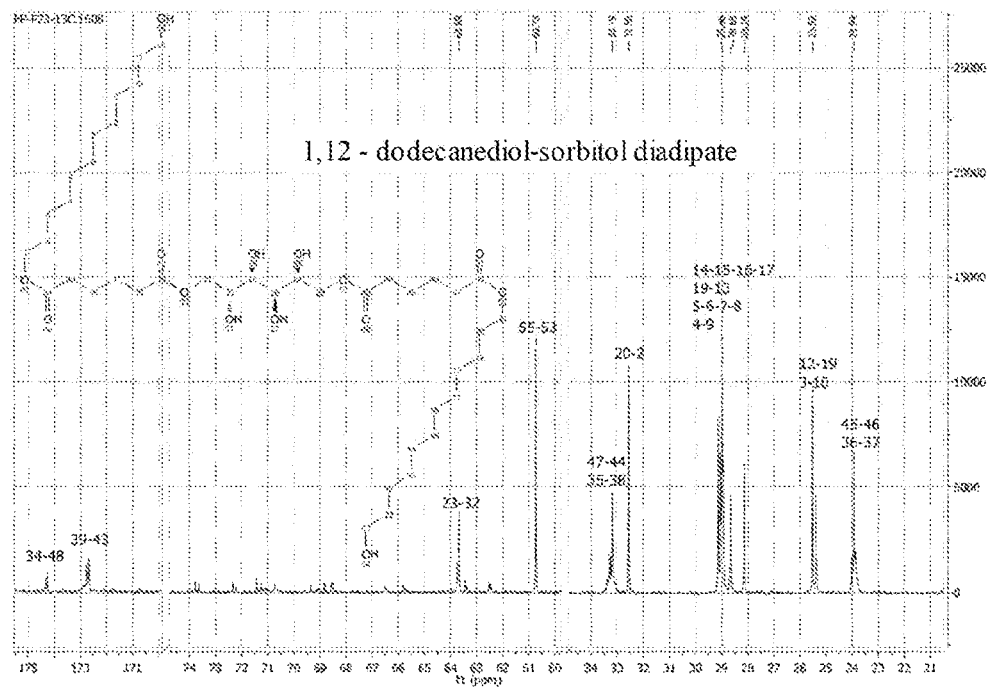
FIG. 2d corresponds to the spectrum of NMR 13C bis (1,12 dodecanediol)-sorbitol diadipate.

Using this data, the chemical structures of the synthesised polyester polyols were determined by the analysis of the spectra obtained (FIGS. 1a to 1d and FIGS. 2a to 2d).

2.1.4 Analysis of the Results via NMR of the Phosphorus 31

The magnetic resonance analysis of the phosphorus 31 of all of the synthesised polyester polyols makes it possible to precisely determine the quantities of residual acid functions in the polyester polyols, as well as the quantity of total hydroxyl functions by overcoming the steric hindrance.

TABLE 2

Hydroxyl and acid indexes determined by NMR-$^{31}$P analyses

| Polyol | Mmol.g$^{-1}$ of OH | HOI | Mmol.g$^{-1}$ of COOH | IA |
| --- | --- | --- | --- | --- |
| 1 | 10.37 | 581.8 | 0.60 | 33.7 |
| 2 | 11.21 | 628.9 | 0.40 | 22.4 |
| 3 | 10.52 | 590.2 | 0.42 | 48 |
| 4 | 9.03 | 506.6 | 0.33 | 18.5 |
| 5 | 8.24 | 462.3 | 0.4 | 22.4 |
| 6 | 7.84 | 439.8 | 0.22 | 12.3 |
| 7 | 8.7 | 488 | 0.20 | 11.22 |

2.1.5 Structure of the Molecules Obtained

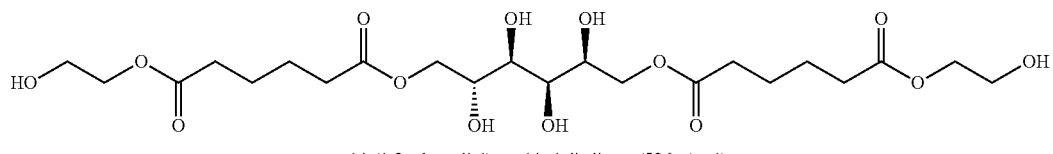

a: bis(1,2 ethanediol)-sorbitol diadipate (526 g/mol)

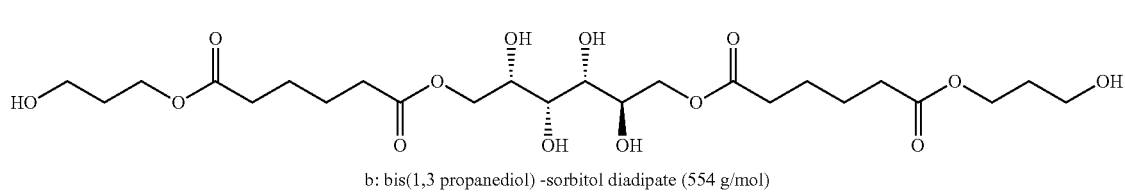

b: bis(1,3 propanediol)-sorbitol diadipate (554 g/mol)

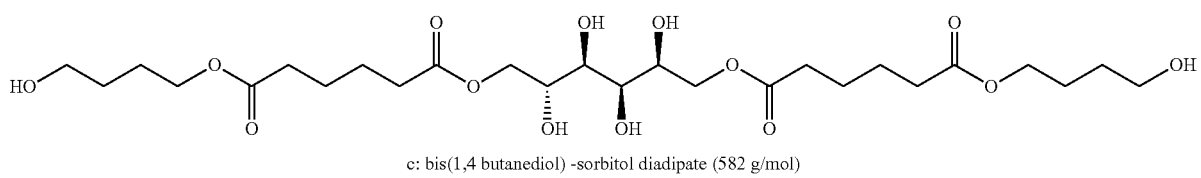

c: bis(1,4 butanediol)-sorbitol diadipate (582 g/mol)

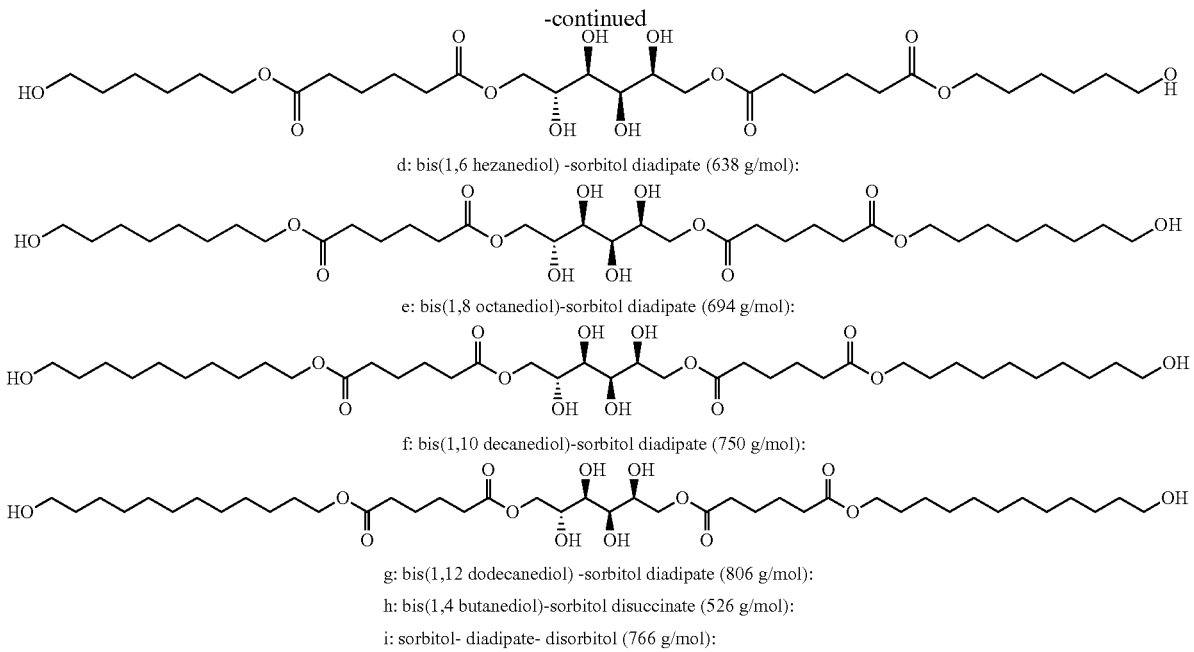

d: bis(1,6 hezanediol)-sorbitol diadipate (638 g/mol):

e: bis(1,8 octanediol)-sorbitol diadipate (694 g/mol):

f: bis(1,10 decanediol)-sorbitol diadipate (750 g/mol):

g: bis(1,12 dodecanediol)-sorbitol diadipate (806 g/mol):

h: bis(1,4 butanediol)-sorbitol disuccinate (526 g/mol):

i: sorbitol- diadipate- disorbitol (766 g/mol):

The carried-out characterisations confirm that the synthesised polyester polyols have a well-defined architecture that is in accordance with the two-step operating protocols used aiming such structure of the molecules. The chemical structures of (a) bis(1,2 ethanediol)-sorbitol diadipate (526 g/mol), (b) bis(1,3propanediol)-sorbitol diadipate (554 g/mol), (c) bis(1,4-butanediol)-sorbitol diadipate (582 g/mol), (d) bis(1,6 hexanediol)-sorbitol diadipate (638 g/mol), (e) bis(1,8 octanediol)-sorbitol diadipate (694 g/mol), (f) bis(1,10 decanediol)-sorbitol diadipate (750 g/mol), (g) bis(1,12 dodecanediol)-sorbitol diadipate (806 g/mol), (h) bis(1,4 butanediol)-sorbitol disuccinate (526 g/mol), (i) sorbitol-diadipate-disorbitol (766 g/mol). The chemical structures of the polyols obtained are found hereinbelow with the general formula $C_aH_bO_c$ with $22 \leq a \leq 42$, $38 \leq b \leq 78$, $14 \leq c \leq 22$.

2.2 Characterisation of the Properties of the Polyester Polyols 2.2.1 DSC Analysis Thermal characterisations of the DSC type make it possible to determine the crystallinity or not of the polyester polyol obtained by measuring a melting temperature (Tf) and a glass transition temperature (Tg). Having amorphous polyester polyols (absence of Tf) with a low Tg (lower than ambient temperature) is particularly advantageous as this ensures that the polyester polyols will not undergo any change in state during the formulation.

TABLE 3

Glass transition (Tg) and melting (Tf) temperatures of the polyols

| Nature of the polyol | Tg (° C.) | Tf (° C.) |
|---|---|---|
| bis(1,2 ethanediol)-sorbitol diadipate | −25 | / |
| bis(1,3 propanediol)-sorbitol diadipate | −27 | / |
| bis(1,4-butanediol)-sorbitol diadipate | −48 | / |
| bis(1,6 hexanediol)-sorbitol diadipate | −53 | / |
| bis(1,8 octaediol)-sorbitol diadipate | / | 23 |
| bis(1,10 decanediol)-sorbitol diadipate | −75 | 0-50 |
| bis(1,12 dodecanediol)-sorbitol diadipate | / | 30-40 |

TABLE 3-continued

Glass transition (Tg) and melting (Tf) temperatures of the polyols

| Nature of the polyol | Tg (° C.) | Tf (° C.) |
|---|---|---|
| bis(1,4 butanediol)-sorbitol disuccinate | −40 | / |
| sorbitol- diadipate- sorbitol | −10 | / |

Thus, among all of the synthesised molecules only three have a melting temperature and are therefore in crystalline form: 1,8 octanediol-sorbitol adipate, 1,10 decanediol-sorbitol adipate and bis(1.12 dodecanediol)-sorbitol diadipate. The other polyols have Tg at temperatures less than 0° C. (see table 3).

The low Tg and the absence of crystallisation and melting temperatures for the following three polyols: bis(1.2 ethanediol)-sorbitol-diadipate, bis(1.3 propanediol)-sorbitol-diadipate and bis(1.4 butanediol)-sorbitol-diadipate make it possible to affirm that these polyols will remain viscous liquids at ambient temperature and therefore in particular at the temperatures of use of the polyurethane foams, the preferred application of the invention (20-25° C.). The other polyols do not have a Tf namely bis (1,6 hexanediol)-sorbitol diadipate, bis (1,4 butanediol)-sorbitol disuccinate and sorbitol-diadipate-sorbitol. They will remain viscous (waxy aspect) at ambient temperature (20-25° C.). The three polyols that have a Tf are both solid at ambient temperature, which indicates a use in an application other than foaming such as for example coating, adhesives or elastomers are recommended. Indeed, during the foaming operations, the polyol must be able to be mixed with a polyisocyanate at 20-30° C., crystalline products with melting temperatures greater than 15° C. are not recommended. Thus, bis(1.2 ethanediol)-sorbitol-diadipate, bis(1.3 propanediol)-sorbitol-diadipate and bis(1.4 butanediol)-sorbitol-diadipate are particularly advantageous in a large panel of applications and more particularly foaming. The other polyester polyols can be intended for applications of the elastomer, adhesive or coating type.

2.2.2 Thermogravimetric Analysis (ATG)

ATG makes it possible to determine the steps of the loss of mass and degradation of the polyester polyols.

The analysis of the results shows a degradation in two steps. Thus, all of the polyols analysed are degraded in two steps (see table 4).

TABLE 4

Degradation temperatures of the polyols

| | 1st degradation | | 2nd |
|---|---|---|---|
| Nature of the polyol | T° C. range | % wt of loss | degradation T° C. range |
| bis(1,2 ethanediol)-sorbitol diadipate | 50-130 | 7 | 150-450 |
| bis(1,3 propanediol)-sorbitol diadipate | 50-135 | 8 | 135-450 |
| bis(1,4-butanediol)-sorbitol diadipate | 40-130 | 7 | 130-450 |
| bis(1,6 hexanediol)-sorbitol diadipate | 40-162 | 11 | 162-450 |
| bis(1,8 octaediol)-sorbitol diadipate | 40-175 | 12 | 175-500 |
| bis(1,10 decanediol)-sorbitol diadipate | 40-200 | 16 | 200-450 |
| bis(1,12 dodecanediol)-sorbitol diadipate | 40-210 | 19 | 210-475 |
| bis(1,4 butanediol)-sorbitol disuccinate | 40-160 | 9 | 160-475 |
| sorbitol- diadipate- sorbitol | 40-125 | 4 | 125-500 |

During the formulation of polyurethane foams, the reaction at play is exothermic and the reaction medium reaches temperatures of 100° C. during the method. The polyester polyols used must therefore be stable up to 100° C.

The first step at about 100° C. corresponds to a loss of mass relative to the loss of residual water in the form of vapour and to the loss still in the form of residual monomer vapour that did not react during the synthesis of the molecule. The loss of these small molecules is not a disadvantage for the formulation of polyurethane foams since they are present in small quantities and are extremely reactive with the isocyanates used in the formulation of polyurethane foams. They would therefore have reacted without incident on the rest of the method before evaporation before the reaction medium reaches 100° C.

The second degradation corresponds to the degradation of the polyester polyol. The degradation mostly described in literature is the scission of the chain via the atom of hydrogen in $\beta$ position of the ester bond, or $\alpha$ (less substantial phenomenon). There will also be intramolecular reactions (backbiting) resulting in cyclisations of chains or in the cyclisation of molecules (coming from a first degradation for example) etc. This corresponds to temperatures at which the polyester polyol will be degraded and lose its properties. Consequently, this temperature is indicative of the stability of the product obtained for these future uses.

All of the synthesised polyester polyols are stable beyond 100° C., they can therefore all be used for the formulation of a foam, of an elastomer, of an adhesive or of a coating with regards to their thermal properties.

2.2.3 Rheological Analysis of the Obtained Products

The rheological studies (table 5) make it possible to determine the viscosity of the synthesised polyols as a function of the temperature and the Newtonian nature or not thereof according to the shear rate.

TABLE 5

Rheological study

| Polyol | Viscosity according to the shear rate at 20° C. | | Viscosity according to the shear rate at 25° C. | |
|---|---|---|---|---|
| | Viscosity (Pa.S) | Type of fluid | Viscosity (Pa.S) | Type of fluid |
| bis(1,3 propanediol))sorbitol diadipate | 125.5 ± 1.7 | Newtonian | 68.2 ± 0.5 | Newtonian |
| bis(1,4 butanediol) sorbitol diadipate | 44.6 ± 1.2 | Newtonian | 24.3 ± 0.2 | Newtonian |
| bis(1,6 hexanediol)-sorbitol diadipate | 48.7 ± 1.2 | Newtonian | 27.16 ± 1.7 | Newtonian |
| bis(1,4 butanediol) sorbitol diadipate modified glycerol | 5.3 ± 0.4 | Newtonian | 3.4 ± 0.2 | Newtonian |
| bis(1,4 butanediol)-sorbitol diadipate modified ratio 2.1 to 1.4 BDO | 12.2 ± 1.5 | Newtonian | 7.3 ± 0.5 | Newtonian |

These results show that the products obtained namely bis(1,4 butanediol)-sorbitol-diadipate, bis(1,6 hexanediol)-sorbitol-diadipate and bis(1,4 butanediol)-sorbitol-diadipate modified glycerol and ratio 2.1 to 1,4 BDO have particularly advantageous characteristics for a use in all of the applications that conventionally use petroleum-sourced products such as foams, elastomers, adhesives or polyurethane coatings due to their sufficiently low viscosity (liquid nature) that allows them to be mixed at ambient temperature with the other components of the formulation. Bis(1,3 propanediol)-sorbitol diadipate has a high viscosity at 20° C., however, its drop in viscosity at 25° C. could allow for the use of this polyester polyol at this temperature in such formulations. The other polyester polyols were not subjected to viscosity analyses at 20° C. and 25° C. because they are waxy (solid) at these temperatures (see table 3) which makes their use in the formulation of polyurethane foams less interesting but has no incidence for the formulations of elastomers, adhesives or coatings since the mixing of the formulation can be carried out at a temperature that is higher than the ambient temperature.

2.2.4 Analysis of the Hydroxyl Index (HOI)

The measurement of the hydroxyl index is used in particular for the elaboration of polyurethane foams. It makes it possible to evaluate the portion of isocyanate in the formulation of polyurethane foam.

The synthesis of polyols comprising many hydroxyl groups of a different nature (primary and secondary) makes the titration difficult in terms of the steric hindrance for the secondary hydroxyl groups placed side by side on the sorbitol groups. Thus the hydroxyl indexes (HOI) presented in table 6 reflect the number of hydroxyls that can be accessed and taken into account for the formulation of polyurethane foam.

TABLE 6

HOI of the synthesised polyols

| Nature of the polyol | HOI (mg KOH/g) |
|---|---|
| bis(1,4 butanediol)-sorbitol disuccinate | 409 |
| sorbitol-diadipate-sorbitol | 692 |
| bis(1,2 ethanediol)-sorbitol diadipate | 533 |
| bis(1,3 propanediol)-sorbitol diadipate | 437 |
| bis(1,4 butanediol)-sorbitol diadipate | 400 |
| bis(1,6 hexanediol)-sorbitol diadipate | 415 |

TABLE 6-continued

HOI of the synthesised polyols

| Nature of the polyol | HOI (mg KOH/g) |
|---|---|
| bis(1,8 octaediol)-sorbitol diadipate | 355 |
| bis(1,10 decanediol)-sorbitol diadipate | 326 |
| bis(1,12 dodecanediol)-sorbitol diadipate | 311 |

The ranges of hydroxyl indexes sought by a manufacturer of foam depends on the type of foams (PUR, PIR, etc.) and on the number of polyols introduced into the formulation. In general, for a rigid foam, the range extends from 100 to 700 mg KOH/g. In the case of a foam of the PUR type the range of the hydroxyl index (HOI) that allows for the obtaining of a crosslinked three-dimensional network is between 300 and 700 mg KOH/g while for a network of the PIR type, the range of HOI has to be between 100 and 500 mg KOH/g. Thus, all of the polyester polyols have hydroxyl indexes that allow them to be used in PUR and PIR formulation.

2.2.5 Acid Titration of the Polyols

The acid titration of the polyols incorporated into rigid polyurethanes foams is used in the formulation of these foams because the residual acid functions of the polyols polyesters are able to inhibit the catalysts used during the formulation of rigid polyurethane foams if the quantity thereof is excessive. The steps of titration and the three types of neutralisations were tested on bis(1,4 butanediol)-sorbitol diadipate because all of the preceding characterisations make it the polyester polyol that is most suitable for the formulation of polyurethane foams in particular rigid polyurethane foams.

Titration before and after neutralisation makes it possible to judge the effectiveness of the latter. The step of neutralisation makes it possible to decrease the acid index by four and even by ten in optimum conditions.

Various points will be noted during the neutralisations with the bases. With soda, the final polyester polyol is whitish while with potash, it is possible to extract a solid acido-basic precipitate and the aspect of the polyester polyol has not changed. The precipitates can always be condensed via centrifugation, but the neutralisation with potash has a certain advantage by facilitating the removal of the potash/acid complex that precipitates as agglomerates of a larger size than those of the soda.

TABLE 7

Acidity index before and after neutralisation

| | After synthesis | Neutralised NaOH | Neutralised KOH | Neutralised hexanol |
|---|---|---|---|---|
| Acid index (mg KOH/g) | 59 ± 2.3 | 8.3 ± 0.4 | 15.9 ± 1.6 | 24.2 ± 2 |

The acidity index of the polyester polyol is evaluated before and after neutralisation. All of the results for bis(1,4 butanediol)-sorbitol diadipate are present in the table 7. The acidity index corresponds to the number of mg of KOH required to neutralise all of the carboxylic acid groups present in one gram of a polyester polyol. The acidity index can be determined by colorimetric dosage with methylene blue by using a potash solution at 0.1 mol/L in the methanol.

The three types of neutralisation make it possible to substantially lower the acidity index of the polyester polyol. This neutralisation allows for the obtaining of a formulation of rigid polyurethane foam of very good quality.

Example 3

Formulation of Polyurethane Foams

Polyurethane foams were obtained by using polyester polyols with a base of bis(1,4 butanediol)-sorbitol-diadipate and neutralised bis(1,4 butanediol)-sorbitol-diadipate. A premix containing the polyol and the various additives and expansion gas is prepared then the necessary quantity of polymeric diisocyante (pMDI) is added thereto (see table 8). The premix is obtained by a successive adding of components between which a step of homogenisation is carried out.

TABLE 8

Formulation of rigid PUR foams

| Supplier Reference | Control PUR | PUR non neut. polyol | KOH 2 parts Cat. amine Neut. | PUR distilled Hexanol Neut. | PUR NaOH Neut. | PUR Hexanol Neut. |
|---|---|---|---|---|---|---|
| | 114.4 | 115.0 | 115.0 | 115.0 | 115. | 115.0 |
| pMDI | 190.14 | 147.38 | 147.29 | 147.29 | 147.29 | 147.29 |
| Control polyol | 100.00 | | | | | |
| Polyol sorbitol base | | 100 | | | | |
| Polyol sorbitol base neut. NaOH | | | | | 100.00 | |
| Polyol sorbitol base neut. KOH | | | 100.00 | | | |
| Polyol sorbitol base neut. Hexanol | | | | | | 100.00 |
| Polyol sorbitol base neut. distilled hexanol | | | | 100.00 | | |
| Water | 1.66 | 1.6 | 1.60 | 1.60 | 1.60 | 1.60 |
| Polyether polysiloxane B1048 surfactant | 2.50 | 2.5 | 2.56 | 2.56 | 2.56 | 2.50 |
| Catalyst: Dimethylcyclohexylamine | 2.35 | 1.7 | 2.00 | 2.06 | 2.06 | 2.11 |
| Flame retardant: TCPP | 10.06 | 10 | 10.00 | 10.00 | 10.0 | 10.05 |
| Swelling agent: Isopentane | 15.37 | 11.92 | 13.08 | 13.52 | 13.9 | 15.73 |
| TOTAL | 322.0 | 275.10 | 276.53 | 277.03 | 277.5 | 279.28 |

In the framework of formulations of rigid polyurethane foams (PUR) four tests were conducted: an industrial control (standard polyether of functionality 3.3 and a hydroxyl index of 585 mg KOH/g), a formulation with the polyester polyol with a base of 1.4 butanediol-sorbitol-adipate neutralised with KOH, then NaOH and neutralised with hexanol. Indeed, this polyester polyol has the best viscosity at ambient temperature and a low production cost (inexpensive monomers and bio-sourced or bio-sourceable) for the formulation of PUR foams.

The premix formulations required to carry out the measurements of the characteristic times are expressed as a number of parts (table 8). To the premix is then added the quantity of polyisocyanate (type 4,4 polymeric MDI) desired (table 8).

The characteristic times for the obtaining of a foam are measured namely the time for cream, string and tack-free as well as the height of the foam (table 9).

TABLE 9

Characteristics of the foam obtained

| Characteristic times in s | Control PUR | PUR non neut. polyol | Neut. With 2 parts KOH Catalyst amine | PUR distilled Hexanol Neut. | PUR NaOH Neut. | PUR Hexanol Neut. |
|---|---|---|---|---|---|---|
| Cream | 10 | 75 | 15 | 50 | 14 | 45 |
| String | 39 | 420 | 70 | 163 | 73 | 203 |
| Tack-free | 60 | 1500 | 115 | 299 | 80 | 346 |
| foam height | 26.1 | 5 | 23.7 | 21.8 | 23.4 | 22.6 |

The characteristic times obtained with the polyester polyols neutralised with potash and with soda are satisfactory, in the case of polyester polyols neutralised with hexanol the times are not as advantageous. Thus, the use of the neutralised polyester polyol, allows in comparison to non-neutralised polyester polyols, for the observation of a better reaction kinematics (shorter) and a foam height that is particularly advantageous, equivalent to non-bio-sourced products (control PUR). It is therefore recommended to use a neutralised version of the polyester polyol for the formulation of rigid polyurethane foams.

Using a polyester polyol with a neutralised sorbitol base, it is therefore possible to formulate a polyurethane foam with kinematic characteristics that are similar to those of the non-bio-sourced products that are currently used. Better quality foams are obtained from polyols neutralised with potash or with soda.

The invention claimed is:

1. A polyester polyol having the general formula Rx-Ry-Rz-Ry'-Rx', wherein:
    Rz is a C4 to C7 sugar alcohol,
    Ry and Ry' are identical or different diesters having formula —OOC—$C_n$—COO— with n between 2 and 10, and
    Rx and Rx' are identical or different C2 to C12 monoalcohols.

2. The polyester polyol according to claim 1, wherein Rz is a C5 or C6 sugar alcohol.

3. The polyester polyol according to claim 1, wherein n is between 3 and 10.

4. The polyester polyol according to claim 1, wherein Rx and Rx' are C3 to C8 monoalcohols.

5. A method for obtaining a polyester polyol according to claim 1, comprising the following steps:

a) a step of polycondensation at a temperature between 110 and 200° C.:
        i. of a sugar alcohol Z in C4 to C7,
        ii. of two diacids Y and Y' in C4 to C12 which are identical or different,
        iii. of two diols X and X' in C2 to C12 which are identical or different,
    b) optionally, a step of neutralisation;
    wherein the step of polycondensation comprises a first polycondensation (a-1) of the sugar alcohol Z and of the diacids Y and Y' and a second polycondensation (a-2) of the product obtained in the first polycondensation (a-1) with the diols X and X'.

6. A polymer comprising the polyester polyol according to claim 1.

7. A composition comprising the polyester polyol according to claim 1, or a polymer comprising said polyester polyol, the polymer being a polyurethane or a polyisocyanurate.

8. The composition according to claim 7, wherein the composition is a foam, an elastomer, an adhesive, a coating or a composition allowing for the obtaining of any one of the foam, elastomer, adhesive and coating after polymerisation.

9. The composition according to claim 7, further comprising a reaction catalyst and a polyisocyanate.

10. A method for obtaining a foam, a coating, an adhesive or a polyurethane or polyisocyanurate elastomer comprising:
    a step of obtaining a polyester polyol according to claim 1,
    a step of adding of at least one polyisocyanate and of at least one reaction catalyst, and
    a step of polymerisation.

11. A composition comprising the polymer of claim 6.

12. The composition according to claim 11, wherein the composition is a foam, an elastomer, an adhesive, a coating or a composition allowing for the obtaining of any one of the foam, elastomer, adhesive and coating after polymerisation.

13. The composition according to claim 11, further comprising a reaction catalyst and a polyisocyanate.

14. A method for obtaining a foam, a coating, an adhesive or a polyurethane or polyisocyanurate elastomer comprising:
    a step of obtaining a polymer according to claim 6,
    a step of adding of at least one polyisocyanate and of at least one reaction catalyst, and
    a step of polymerisation.

15. The method according to claim 5, comprising the following step:
    a) a step of polycondensation at a temperature between 110 and 200° C. for 5 to 10 hours:
        i. of a sugar alcohol Z in C5 or C6,
        ii. of two diacids Y and Y' in C5 to C12 which are identical or different,
        iii. of two diols X and X' in C3 to C8 which are identical or different.

16. The polymer according to claim 6, the polymer being a polyurethane or a polyisocyanurate.

17. The polyester polyol according to claim 1, wherein n is between 4 and 10.

18. The polyester polyol according to claim 1, wherein Rx and Rx' are C4 monoalcohols.

19. The method according to claim 5, wherein the sugar alcohol Z is chosen from erythritol, arabitol, ribitol, xylitol, sorbitol, dulcitol, mannitol, and volemitol.

20. The method according to claim 5, wherein the diacids Y and Y' are independently chosen from butanedioic acid, pentanedioic acid, hexanedioic acid, heptanedioic acid, octanedioic acid, nonanedioic acid, decanedioic acid, undecanedioic acid, dodecanedioic acid, and mixtures thereof.

21. The method according to claim 5, wherein the diols X and X' are independently chosen from 1,2-ethanediol, 1,3-propanediol, 1,4-butanediol, 1,6-hexanediol, 1,8-octanediol, 1,10-decanediol, 1,12-dodecanediol, and mixtures thereof.

\* \* \* \* \*